United States Patent [19]

Kanellakopulos et al.

[11] Patent Number: 5,525,622
[45] Date of Patent: Jun. 11, 1996

[54] SUBSTITUTED PYRAZOLINES

[75] Inventors: Johannes Kanellakopulos, Hilden; Rainer Fuchs, Wuppertal; Christoph Erdelen, Leichlingen, all of Germany

[73] Assignee: Bayer Aktiengesellschaft, Leverkusen, Germany

[21] Appl. No.: 28,490

[22] Filed: Mar. 9, 1993

Related U.S. Application Data

[63] Continuation-in-part of Ser. No. 934,086, Aug. 21, 1992, abandoned, and Ser. No. 934,087, Aug. 21, 1992, abandoned.

[30] Foreign Application Priority Data

| Aug. 28, 1991 | [DE] | Germany | 41 28 564.6 |
| May 29, 1992 | [DE] | Germany | 42 17 862.2 |
| May 29, 1992 | [DE] | Germany | 42 17 863.0 |

[51] Int. Cl.$^6$ ............. A01N 43/56; C07D 231/40; C07D 403/04
[52] U.S. Cl. ............. 514/403; 548/364.1; 548/371.7
[58] Field of Search ............. 548/364.1, 371.7; 514/403

[56] References Cited

U.S. PATENT DOCUMENTS

| 4,663,341 | 5/1987 | Jacobson | 514/403 |
| 4,863,947 | 9/1989 | Jacobson | 514/403 |
| 5,109,014 | 4/1992 | Jacobson | 514/403 |

*Primary Examiner*—Robert W. Ramsuer
*Attorney, Agent, or Firm*—Sprung Horn Kramer & Woods

[57] ABSTRACT

There are provided new substituted pyrazolines of the general formula (I)

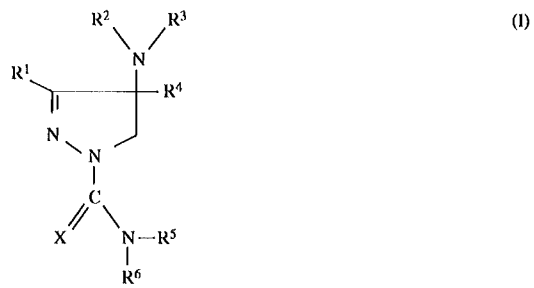

in which
$R^1$ represents optionally substituted phenyl and either
$R^2$ represents a radical of the formula $-CO-R^7$, $-COOR^7$ or $-SO_2-R^7$,
where $R^7$ has the meaning given in the text of the application, and
$R^3$ represents hydrogen, alkyl or halogenoalkyl or
$R^2$ and $R^3$ together with the nitrogen atom to which they are bonded represent a heterocycle
$R^4$ represents hydrogen, alkyl, halogenoalkyl, halogenoalkylthio, halogen, alkoxycarbonyl or in each case optionally substituted cycloalkyl or aryl,
$R^5$ represents hydrogen or alkyl,
$R^6$ represents in each case optionally substituted alkyl, cycloalkyl or 3,4-disubstituted phenyl and
X represents oxygen or sulphur.

The new substituted pyrazolines have a highly pronounced activity against animal pests, in particular against insects.

10 Claims, No Drawings

SUBSTITUTED PYRAZOLINES

This application is a continuation-in-part of application Ser. No. 07/934,086, filed Aug. 21, 1992, now abandoned and a continuation-in-part of application Ser. No. 07/934,087, filed Aug. 21, 1992, now abandoned.

The invention relates to new substituted pyrazolines, to a plurality of processes for their preparation, and to their use as pesticides.

It has been disclosed that certain substituted pyrazolines have insecticidal properties (cf., for example, DE-A 2,700,258; DE-A 2,529,689; U.S. Pat. No. 4,174,393).

However, the level or duration of action of these previously known compounds is not entirely satisfactory in all fields of application, in particular in the case of certain insects or when low concentrations are applied.

New substituted pyrazolines of the general formula (I) have been found,

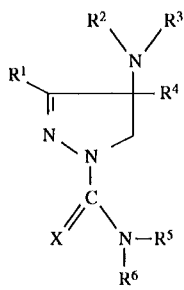

in which
R¹ represents optionally substituted phenyl and either
R² represents a radical of the formula —CO—R⁷, —COOR⁷ or —SO₂—R⁷, and
R³ represents hydrogen, alkyl or halogenoalkyl or
R² and R³ together with the nitrogen atom to which they are bonded represent a heterocycle of the formula

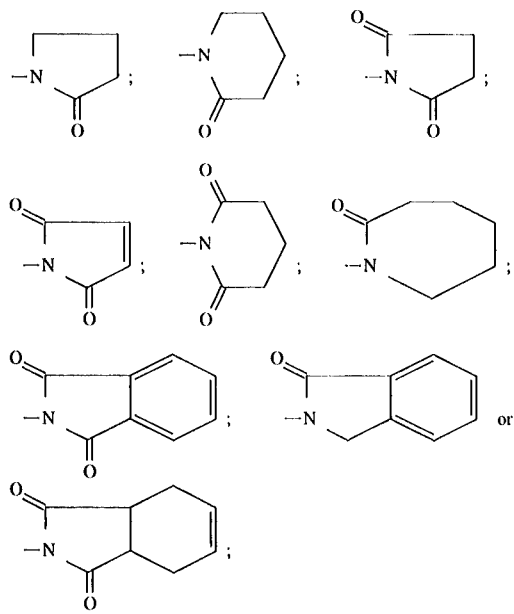

R⁴ represents hydrogen, alkyl, halogenoalkyl, halogenoalkylthio, halogen, alkoxycarbonyl or in each case optionally substituted cycloalkyl or aryl,
R⁵ represents hydrogen or alkyl,
R⁶ represents in each case optionally substituted alkyl, cycloalkyl or 3,4-disubstituted phenyl and X represents oxygen or sulphur, where
R⁷ represents hydrogen, alkyl, alkenyl, alkinyl, halogenoalkyl, halogenoalkenyl, halogenoalkinyl, alkoxyalkyl, alkylthioalkyl, nitroalkyl, cyanoalkyl, alkoxycarbonylalkyl, in each case optionally substituted cycloalkyl, aralkyl, aryl or heterocyclyl or a radical

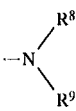

in which either
R⁸ represents hydrogen or alkyl and
R⁹ represents alkyl or in each case optionally substituted aralkyl or aryl, or
R⁸ and R⁹ together with the nitrogen atom to which they are bonded represent an optionally substituted heterocycle which can, if appropriate, contain further hetero atoms.

Depending on the nature of the substituents, the compounds of the formula (I) may optionally exist in the form of geometric and/or optical isomers or isomer mixtures of various compositions. The invention claims the pure isomers as well as the isomer mixtures.

Furthermore, it has been found that the new substituted pyrazolines of the general formula (I)

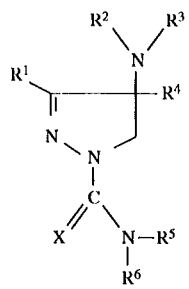

R¹ represents optionally substituted phenyl and either
R² represents a radical of the formula —CO—R⁷, —COOR⁷ or —SO₂—R⁷, and
R³ represents hydrogen, alkyl or halogenoalkyl or
R² and R³ together with the nitrogen atom to which they are bonded represent a heterocycle of the formula

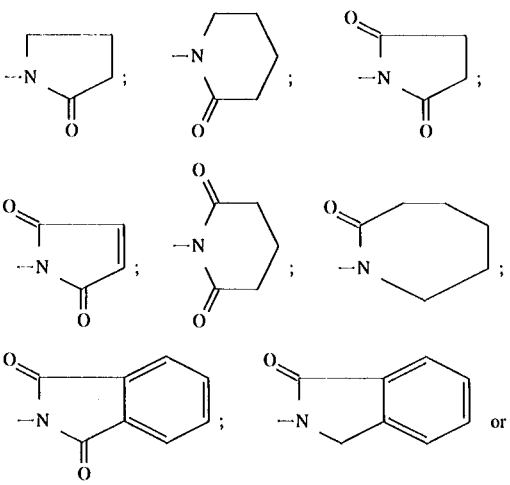

-continued

R⁴ represents hydrogen, alkyl, halogenoalkyl, halogenoalkylthio, halogen, alkoxycarbonyl or in each case optionally substituted cycloalkyl or aryl, R⁵ represents hydrogen or alkyl, R⁶ represents in each case optionally substituted alkyl, cycloalkyl or 3,4-disubstituted phenyl and X represents oxygen or sulphur, where R⁷ represents hydrogen, alkyl, alkenyl, alkinyl, halogenoalkyl, halogenoalkenyl, halogenoalkinyl, alkoxyalkyl, alkylthioalkyl, nitroalkyl, cyanoalkyl, alkoxycarbonylalkyl, in each case optionally substituted cycloalkyl, aralkyl, aryl or heterocyclyl or a radical $$-N\begin{matrix}R^8\\R^9\end{matrix}$$

in which either

R⁸ represents hydrogen or alkyl and

R⁹ represents alkyl or in each case optionally substituted aralkyl or aryl, or

R⁸ and R⁹ together with the nitrogen atom to which they are bonded represent an optionally substituted heterocycle which can, if appropriate, contain further hetero atoms, are obtained when pyrazolines of the formula (II) which are unsubstituted in the 1-position (II)

in which

R¹, R², R³ and R⁴ have the abovementioned meaning, are reacted either a) with iso(thio)cyanates of the formula (III)

R₆—N=C=X (III)

in which

R⁶ and X have the abovementioned meaning, or b) with (thio)carbamoyl chlorides of the formula (IV)

(IV)

in which

R⁵, R⁶ and X have the abovementioned meaning, if appropriate in the presence of a diluent and if appropriate in the presence of a reaction auxiliary.

Finally, it has been found that the new substituted pyrazolines of the general formula (I) have a good activity against animal pests.

Surprisingly, the substituted pyrazolines of the general formula (I) according to the invention show a considerably better insecticidal activity compared with the compounds which are known from the prior art and which are similar chemically and/or from the point of view of their action.

Formula (I) provides a general definition of the substituted pyrazolines according to the invention. Preferred compounds of the formula (I) are those in which R¹ represents phenyl which is optionally monosubstituted or polysubstituted by identical or different substituents, suitable substituents being: halogen, cyano, nitro, in each case straight-chain or branched alkyl, alkoxy, alkylthio, alkylsulphinyl or alkylsulphonyl, each of which has 1 to 8 carbon atoms, in each case straight-chain or branched halogenoalkyl, halogenoalkoxy, halogenoalkylthio, halogenoalkylsulphinyl or halogenoalkylsulphonyl, each of which has 1 to 8 carbon atoms and 1 to 17 identical or different halogen atoms, in each case straight-chain or branched alkenyl, alkinyl, alkenyloxy or alkinyloxy, each of which has 2 to 8 carbon atoms, in each case straight-chain or branched alkoxycarbonyl or alkoximinoalkyl, each of which has 1 to 8 carbon atoms in the individual alkyl moieties, straight-chain or branched halogenoalkoxycarbonyl having 1 to 9 carbon atoms and 1 to 17 identical or different halogen atoms, divalent dioxyalkylene which has 1 to 4 carbon atoms and which is optionally monosubstituted or polysubstituted by identical or different substituents from the series comprising halogen and/or straight-chain or branched alkyl having 1 to 4 carbon atoms, or phenyl, phenoxy or phenylthio, each of which is optionally monosubstituted or polysubstituted by identical or different substituents from the series comprising halogen and/or straight-chain or branched alkyl having 1 to 4 carbon atoms; and either R² represents a radical of the formula —CO—R⁷, —COOR⁷ or —SO₂—R⁷ and R³ represents hydrogen, straight-chain or branched alkyl having 1 to 8 carbon atoms or straight-chain or branched halogenoalkyl having 1 to 8 carbon atoms and 1 to 17 identical or different halogen atoms, or R² and R³ together with the nitrogen atom to which they are bonded represent a heterocycle of the formula

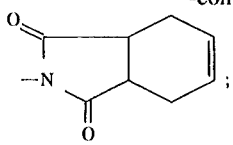

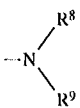

and either

R[8] represents hydrogen or straight-chain or branched alkyl having 1 to 8 carbon atoms, and R[9] represents straight-chain or branched alkyl having 1 to 8 carbon atoms or aralkyl which has 1 to 6 carbon atoms in the straight-chain or branched alkyl moiety and 6 or 10 carbon atoms in the aryl moiety or aryl which has 6 or 10 carbon atoms, each of which is optionally monosubstituted or polysubstituted in the aryl moiety by identical or different substituents, suitable aryl substituents in each case being those mentioned in the case of R[1], or R[8] and R[9] together with the nitrogen atom to which they are bonded represent a saturated or unsaturated, optionally benzo-fused five- to seven-membered heterocycle which can optionally contain 1 to 3 further hetero atoms (in particular nitrogen, oxygen and/or sulphur) and/or 1 to 3 keto groups and which is optionally monosubstituted or polysubstituted by identical or different substituents, suitable substituents being those mentioned in the case of R[1].

Particularly preferred compounds of the formula (I) are those in which

R[1] represents phenyl which is optionally monosubstituted to trisubstituted by identical or different substituents, suitable substituents being: halogen, cyano, nitro, in each case straight-chain or branched alkyl, alkoxy, alkylthio, alkylsulphinyl or alkylsulphonyl, each of which has 1 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms, in each case straight-chain or branched alkenyl, alkinyl, alkenyloxy or alkinyloxy, each of which has 2 to 6 carbon atoms, in each case straight-chain or branched alkoxycarbonyl or alkoximinoalkyl, each of which has 1 to 4 carbon atoms in the individual alkyl moieties, straight-chain or branched halogenoalkoxycarbonyl having 1 to 5 carbon atoms and 1 to 9 identical or different halogen atoms, or divalent dioxyalkylene which has 1 to 3 carbon atoms and is optionally monosubstituted or polysubstituted by identical or different substituents from the series comprising halogen and/or straight-chain or branched alkyl having 1 to 3 carbon atoms, and phenyl, phenoxy or phenylthio, each of which is optionally monosubstituted or polysubstituted by identical or different substituents from the series comprising halogen and/or straight-chain or branched alkyl having 1 to 4 carbon atoms; and either R[2] represents a radical of the formula —CO—R[7], —COOR[7] or —SO$_2$—R[7] and R[3] represents hydrogen, straight-chain or branched alkyl having 1 to 6 carbon atoms or straight-chain or branched halogenoalkyl having 1 to 6 carbon atoms and 1 to 13 identical or different halogen atoms, or R[4] represents hydrogen, straight-chain or branched alkyl having 1 to 8 carbon atoms, straight-chain or branched alkoxycarbonyl having 1 to 9 carbon atoms, cycloalkyl which has 3 to 7 carbon atoms and which is optionally monosubstituted or polysubstituted by identical or different alkyl substituents, straight-chain or branched and having 1 to 4 carbon atoms, or represents phenyl which is optionally monosubstituted or polysubstituted by identical or different substituents, suitable substituents being those mentioned in the case of R[1], or represents straight-chain or branched halogenoalkyl or halogenoalkylthio, each of which has 1 to 8 carbon atoms and 1 to 17 identical or different halogen atoms, or represents fluorine, chlorine, bromine or iodine;

R[5] represents hydrogen or straight-chain or branched alkyl having 1 to 8 carbon atoms;

R[6] represents straight-chain or branched alkyl having 1 to 8 carbon atoms, straight-chain or branched halogenoalkyl having 1 to 8 carbon atoms and 1 to 17 identical or different halogen atoms, cycloalkyl which has 3 to 7 carbon atoms and which is optionally monosubstituted or polysubstituted by identical or different substituents from the series comprising halogen and/or in each case straight-chain or branched alkyl or halogenoalkyl, each of which has 1 to 6 carbon atoms and, in the case of the halogenoalkyl, 1 to 13 identical or different halogen atoms, or represents phenyl which is substituted in the 3,4-position, suitable phenyl substituents being those mentioned in the case of R[1], and X represents oxygen or sulphur, where R[7] represents hydrogen, in each case straight-chain or branched alkyl, alkenyl or alkinyl, each of which has up to 8 carbon atoms, in each case straight-chain or branched halogenoalkyl, halogenoalkenyl or halogenoalkinyl, each of which has up to 8 carbon atoms and 1 to 17 identical or different halogen atoms, in each case straight-chain or branched alkoxyalkyl, alkylthioalkyl, nitroalkyl, cyanoalkyl or alkoxycarbonylalkyl, each of which has 1 to 6 carbon atoms in the individual alkyl moieties, or represents cycloalkyl which has 3 to 7 carbon atoms and which is optionally monosubstituted or polysubstituted by identical or different alkyl substituents, straight-chain or branched and having 1 to 4 carbon atoms, or represents aralkyl which has 1 to 6 carbon atoms in the straight-chain or branched alkyl moiety and 6 or 10 carbon atoms in the aryl moiety, aryl which has 6 or 10 carbon atoms or hetero-cyclyl which has 2 to 9 carbon atoms and 1 to 5 identical or different hetero atoms (in particular nitrogen, oxygen and/or sulphur), each of which is optionally monosubstituted or polysubstituted in the aryl or heterocyclyl moiety by identical or different substituents, suitable aryl or heterocyclyl substituents being those mentioned in the case of R[1] or represents a radical of the formula $R^2$ and $R^3$ together with the nitrogen atom to which they are bonded represent a heterocycle of the formula

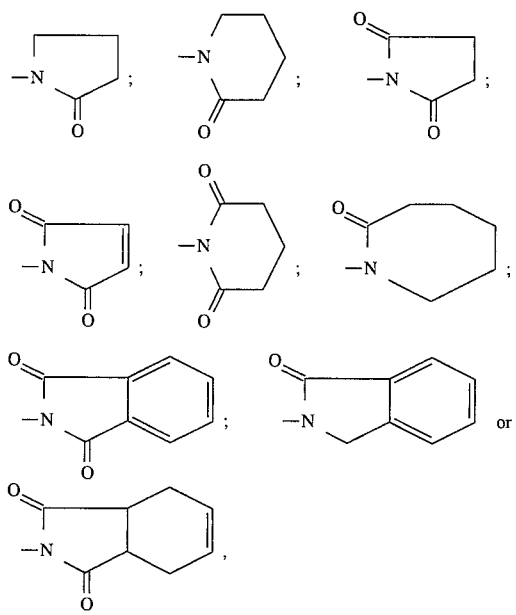

or a six-membered heterocycle which can optionally contain 1 or 2 further hetero atoms (in particular nitrogen, oxygen and/or sulphur) and/or 1 to 3 keto groups, suitable substituents being those mentioned in the case of $R^1$;

$R^4$ represents hydrogen, straight-chain or branched alkyl having 1 to 6 carbon atoms, straight-chain or branched alkoxycarbonyl having 1 to 5 carbon atoms, cycloalkyl which has 3 to 6 carbon atoms and which is optionally monosubstituted to tetrasubstituted by identical or different alkyl substituents, straight-chain or branched and having 1 to 3 carbon atoms, or represents phenyl which is optionally monosubstituted to trisubstituted by identical or different substituents, suitable substituents being those mentioned in the case of $R^1$, or represents straight-chain or branched halogenoalkyl or halogenoalkylthio, each of which has 1 to 6 carbon atoms and 1 to 13 identical or different halogen atoms, or represents fluorine, chlorine or bromine;

$R^5$ reprsents hydrogen or straight-chain or branched alkyl having 1 to 6 carbon atoms;

$R^6$ represents straight-chain or branched alkyl having 1 to 6 carbon atoms, straight-chain or branched halogenoalkyl having 1 to 6 carbon atoms and 1 to 13 identical or different halogen atoms, cycloalkyl which has 3 to 6 carbon atoms and which is optionally monosubstituted to tetrasubstituted by identical or different substituents from the series comprising halogen and/or in each case straight-chain or branched alkyl or halogenoalkyl, each of which has 1 to 3 carbon atoms and, in the case of the halogenoalkyl, 1 to 7 identical or different halogen atoms, or represents 3,4-disubstituted phenyl, suitable phenyl substituents being those mentioned in the case of $R^1$, and X represents oxygen or sulphur, where $R^7$ represents hydrogen, in each case straight-chain or branched alkyl, alkenyl or alkinyl, each of which has up to 6 carbon atoms, in each case straight-chain or branched halogenoalkyl, halogenoalkenyl or halogenoalkinyl, each of which has up to 6 carbon atoms and 1 to 13 identical or different halogen atoms, in each case straight-chain or branched alkoxyalkyl, alkylthioalkyl, nitroalkyl, cyanoalkyl or alkoxycarbonylalkyl, each of which has 1 to 4 carbon atoms in the individual alkyl moieties, cycloalkyl which has 3 to 6 carbon atoms and which is optionally monosubstituted to tetrasubstituted by identical or different alkyl substituents, straight-chain or branched and having 1 to 3 carbon atoms, or represents aralkyl which has 1 to 4 carbon atoms in the straight-chain or branched alkyl moiety and 6 or 10 carbon atoms in the aryl moiety, aryl which has 6 or 10 carbon atoms or heterocyclyl which has 2 to 9 carbon atoms and 1 to 4 identical or different hetero atoms (in particular nitrogen, oxygen and/or sulphur), each of which is optionally monosubstituted to trisubstituted in the aryl or heterocyclyl moiety by identical or different substituents, suitable aryl or heterocyclyl substituents being those mentioned in the case of $R^1$ or represents a radical of the formula

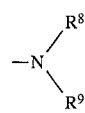

and either $R^8$ represents hydrogen or straight-chain or branched alkyl having 1 to 6 carbon atoms and $R^9$ represents straight-chain or branched alkyl having 1 to 6 carbon atoms or aralkyl which has 1 to 4 carbon atoms in the straight-chain or branched alkyl moiety and 6 or 10 carbon atoms in the aryl moiety or aryl which has 6 or 10 carbon atoms, each of which is optionally monosubstituted to trisubstituted in the aryl moiety by identical or different substituents, suitable aryl substituents in each case being those mentioned in the case of $R^1$, or $R^8$ and $R^9$ together with the nitrogen atom to which they are bonded represent a saturated or unsaturated, optionally benzo-fused, five- or six-membered heterocycle which can optionally contain 1 or 2 further hetero atoms (in particular nitrogen, oxygen and/or sulphur) and/or 1 to 3 keto groups and which is optionally monosubstituted to trisubstitued by identical or different substituents, suitable substituents being those mentioned in the case of $R^1$.

Very particularly preferred compounds of the formula (I) are those in which $R^1$ represents phenyl which is optionally monosubstituted or disubstituted by identical or different substituents, especially suitable substituents being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, trifluoromethyl, difluoromethyl, trifluoromethoxy, difluoromethoxy, difluorochloromethoxy, dichlorofluoromethoxy, trichloromethoxy, tetrafluoroethoxy, pentafluoroethoxy, trichlorodifluoroethoxy, dichlorotrifluoroethoxy, pentachloroethoxy, trifluoromethylthio, difluoromethylthio, dichlorofluoromethylthio, difluorochloromethylthio, trifluoromethylsulphinyl, trifluoromethylsulphonyl, allyl, propargyl, allyloxy, propargyloxy, methoxycarbonyl, ethoxycarbonyl, n- or i-propoxycarbonyl, n-, i-, s- or t-butoxycarbonyl, trifluoromethoxycarbonyl, methoximinomethyl, methoximinoethyl, ethoximinomethyl, ethoximinoethyl, dioxymethylene, difluorodioxymethylene, dioxyethylene, tetrafluorodioxyethylene, trifluorodioxyethylene, difluorodioxyethylene, or phenyl, phenoxy or phenylthio, each of which is optionally monosubstituted to trisubstituted by identical or different substituents from the series comprising fluorine, chlorine, bromine, methyl and/or ethyl; and either $R^2$ represents a radical of the formula —CO—$R^7$, —COOR$^7$ or —SO$_2$—R$^7$ and $R^3$ represents hydrogen, methyl, ethyl, n- or i-propyl or n-, i-, s- or t-butyl, or $R^2$ and $R^3$ together with the carbon atom to which they are bonded represent a heterocycle of the formula

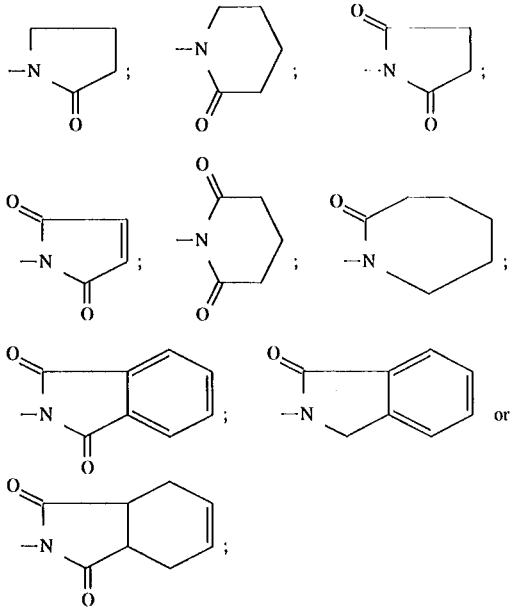

$R^4$ represents hydrogen, methyl or ethyl;

$R^5$ represents hydrogen, methyl or ethyl;

$R^6$ represents n-, i-, s- or t-butyl, or represents cyclohexyl which is optionally monosubstituted or disubstituted by identical or different substituents from the series comprising methyl, ethyl, n- or i-propyl and/or trifluoromethyl, or represents 3,4-disubstituted phenyl, suitable substituents being those mentioned in the case of $R^1$, and X represents oxygen or sulphur, where $R^7$ represents hydrogen, methyl, ethyl, n- or i-propyl, n-, i-, s- or t-butyl, allyl, propargyl, halogenoalkyl having 1 or 2 carbon atoms and 1 to 5 identical or different halogen atoms, or represents alkoxyalkyl or alkylthioalkyl, each of which has 1 or 2 carbon atoms in the individual alkyl moieties, or represents cyclopropyl, cyclopentyl or cyclohexyl, each of which is optionally monosubstituted or disubstituted by identical or different substituents from the series comprising methyl, ethyl and/or n- or i-propyl, or represents phenyl, pyridyl or furanyl, each of which is optionally monosubstituted or disubstituted by identical or different substituents, suitable substituents in each case being those mentioned in the case of $R^1$, or represents a radical of the formula

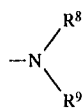

and either $R^8$ represents hydrogen, methyl, ethyl, n- or i-propyl or n-, i-, s- or t-butyl and $R^9$ represents methyl, ethyl, n- or i-propyl, n-, i-, s- or t-butyl, or represents benzyl or phenyl, each of which is optionally monosubstituted or disubstituted by identical or different substituents, suitable substituents in each case being those mentioned in the case of $R^1$, or $R^8$ and $R^9$ together with the carbon atom to which they are bonded represent a heterocycle of the formula

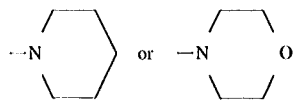

each of which is optionally monosubstituted or disubstituted by methyl.

Especially preferred compounds of the formula (I) are those in which $R^1$ represents phenyl which is optionally monosubstituted or disubstituted by identical or different substituents, especially suitable substituents being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, trifluoromethyl, difluoromethyl, trifluoromethoxy, difluoromethoxy, difluorochloromethoxy, dichlorofluoromethoxy, trichloromethoxy, tetrafluoroethoxy, pentafluoroethoxy, trichlorodifluoroethoxy, dichlorotrifluoroethoxy, pentachloroethoxy, trifluoromethylthio, difluoromethylthio, dichlorofluoromethylthio, difluorochloromethylthio, trifluoromethylsulphinyl, trifluoromethylsulphonyl, allyl, propargyl, allyloxy, propargyloxy, methoxycarbonyl, ethoxycarbonyl, n- or i-propoxycarbonyl, n-, i-, s- or t-butoxycarbonyl, trifluoromethoxycarbonyl, methoximinomethyl, methoximinoethyl, ethoximinomethyl, ethoximinoethyl, dioxymethylene, difluorodioxymethylene, dioxyethylene, tetrafluorodioxyethylene, trifluorodioxyethylene, difluorodioxyethylene, or phenyl, phenoxy or phenylthio, each of which is optionally monosubstituted to trisubstituted by identical or different substituents from the series comprising fluorine, chlorine, bromine, methyl and/or ethyl; and either $R^2$ represents a radical —COR$^7$ and $R^3$ represents hydrogen or methyl or $R^2$ and $R^3$ together with the nitrogen atom to which they are bonded represent a heterocycle of the formula

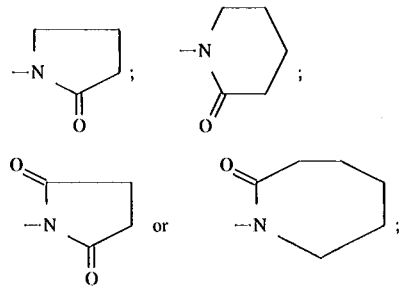

$R^4$ represents hydrogen, $R^5$ represents hydrogen or methyl, $R^6$ represents cyclohexyl which is optionally monosubstituted or disubstituted by identical or different substituents from the series comprising methyl and/or trifluoromethyl, or represents 3,4-disubstituted phenyl, suitable substituents being those mentioned in the case of $R^1$, and X represents oxygen, where $R^7$ represents hydrogen, methyl, ethyl, n- or i-propyl, n-, i-, s- or t-butyl or cyclohexyl, or represents phenyl which is optionally monosubstituted or disubstituted by identical or different substituents, suitable substituents being those mentioned in the case of $R^1$.

Reference may be made to the compounds mentioned individually in the preparation examples.

If, for example, 3-(4-chlorophenyl)-4-[(2-chlorophenyl)carbonylamino]-4,5-dihydropyrazole and 3-chloro-4-trifluoromethylphenyl isocyanate are used as starting materials, the course of process (a) according to the invention can be represented by the following equation:

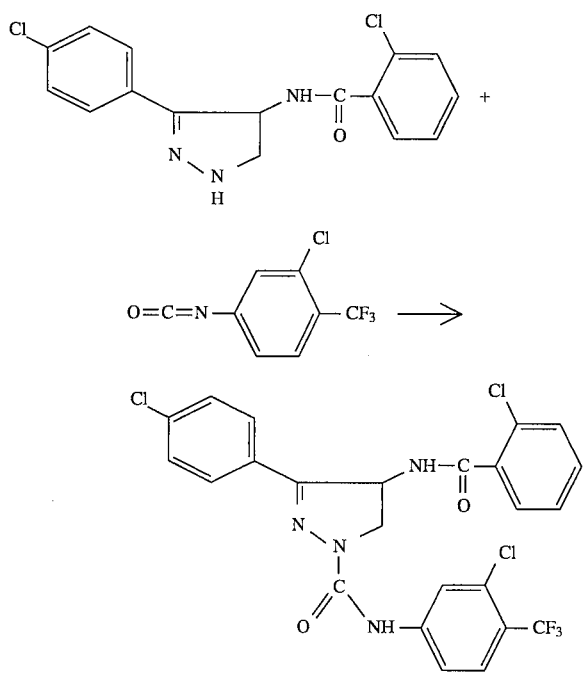

If, for example, 3-(4-chlorophenyl)-4-[(2-chlorophenyl)carbonylamino]-4,5-dihydropyrazole and N-methyl-N-(3-chloro- 4-trifluoromethylphenyl)-carbamoyl chloride are used as starting materials, the course of process (b) according to the invention can be represented by the following equation:

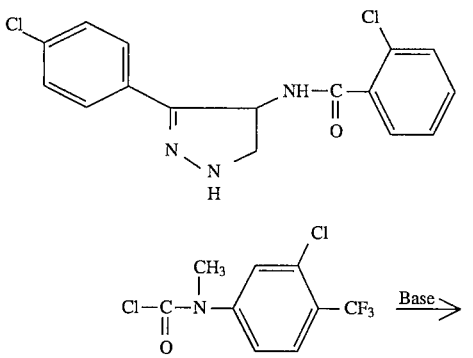

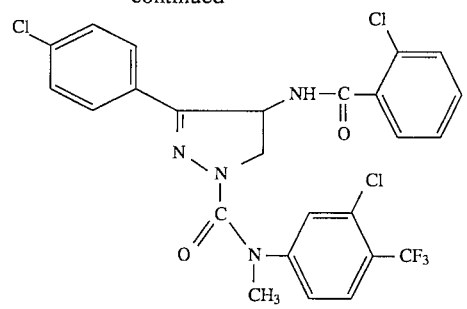

Formula (II) provides a general definition of the pyrazolines which are unsubstituted in the 1-position, which are required as starting materials for carrying out processes (a) and (b) according to the invention. In this formula (II), $R^1$, $R^2$, $R^3$ and $R^4$ preferably represent those radicals which have already been mentioned in connection with the description of the compounds of the formula (I) according to the invention as being preferred for these substituents.

The pyrazolines of the formula (II) which are unsubstituted in the 1-position were hitherto unknown and also a subject of the present invention. They are obtained, for example, when phenacylamine derivatives of the formula (V)

in which
$R^1$, $R^2$, $R^3$ and $R^4$ have the abovementioned meaning are reacted with dimethylmethyleneimmonium chloride, of the formula (VI),

if appropriate in the presence of a diluent such as, for example, acetonitrile, at temperatures between 30° C. and 80° C., and, in a subsequent 2nd step, resulting phenacyldiamine derivatives of the formula (VII)

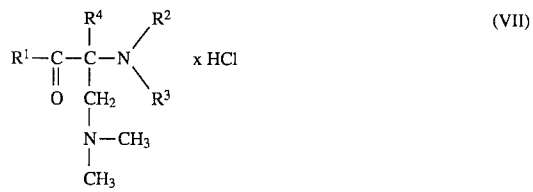

in which
$R^1$, $R^2$, $R^3$ and $R^4$ have the abovementioned meaning, are reacted with hydrazine hydrate at temperatures between 30° C. and 80° C., if appropriate in the presence of a diluent such as, for example, acetonitrile.

In this context, it is also possible and may be advantageous to carry out the reaction of the phenacylamine derivatives of the formula (V) with dimethylmethyleneimmonium chloride, of the formula (VI), and the subsequent reaction of the resulting phenacyldiamine derivatives of the formula (VII) with hydrazine hydrate in one reaction step, in a so-called "one-pot process".

Pyrazolines of the formula (IIa) which are unsubstituted in the 1-position

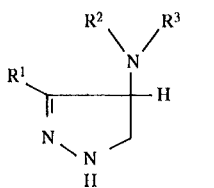

in which
R¹, R² and R³ have the abovementioned meaning are alternatively obtained when phenacylamine derivatives of the formula (Va)

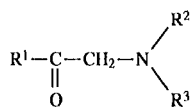

in which
R¹, R² and R³ have the abovementioned meaning are initially reacted, in a first step, with formaldehyde at temperatures between 30° C. and 80° C., if appropriate in the presence of a diluent such as, for example ethanol, and the resulting phenacyl-enamine derivatives of the formula (VIII)

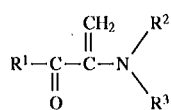

in which
R¹, R² and R³ have the abovementioned meaning, are subsequently reacted with hydrazine hydrate at temperatures between 30° C. and 80° C., if appropriate in the presence of a diluent such as, for example, ethanol.

In this context, it is also possible and may be advantageous to carry out the reaction of the phenacylamine derivatives of the formula (Va) with formaldehyde and the subsequent reaction of the resulting phenacyl-enamine derivatives of the formula (VIII) with hydrazine hydrate in one reaction step, in a so-called "one-pot process".

Phenacylamine derivatives of the formulae (V) and (Va) are known or can be obtained in analogy to known processes (cf., for example, Chem. Ber. 122, 295–300 [1989]; J. Med. Chem. 29, 333–341 [1986]; J. Amer. Chem. Soc. 98, 3621–3627 [1976]; Tetrahedron 31, 2145–2149 [1975]; Zh. Org. Khim. 10, 2429–2436 [1974]; J. Org. Chem. 55, 3658–3660 [1990]; Chem. Ind. 1975, 177; Synthesis 1990, 520).

Dimethylmethyleneimmonium chloride, of the formula (VI), is known (cf., for example, J. Org. Chem. 47, 2940–2944 [1982]; Bull. Soc. Chim. Fr. 1970, 2707–2711).

Some of the phenacyldiamine derivatives of the formula (VII) are known (cf., for example, U.S. Pat. No. 2,980,674 [1957] or CA 56: 3419 [1962]).

Phenacyl-enamine derivatives of the formula (VIII) are known or can be obtained in analogy to known processes (cf., for example, Chem. Ber. 93, 387–391 [1960]; Sankyo Kenkyusho Nemp 15, 36 [1963] or Chem. Abstr. 60: 11876d [1964]; J. Med. Chem. 30, 1497–1502 [1987]; JP 61-053,239; U.S. Pat. No. 4,277,420; Chem. Abstr. 87: 67928y; Khim.-Farm. Zh. 9, 21–24 [1975] or CA 83: 58351v; Collect. Czech. Commun. 19, 317–328 [1954]; Ann. Chim. 46, 267–269 [1956]; J. Chem. Soc. 1953, 4066–4073; Zh. Obshch. Khim. 30, 3714 [1960]; Pharm. Chem. J. 9, 301–304 [1975]).

Formula (III) provides a general definition of the iso(thio)cyanates required as starting materials for carrying out process (a) according to the invention. In this formula (III), R⁸ and X preferably represent those radicals which have already been mentioned in connection with the description of the compounds of the formula (I) according to the invention as being preferred for these substituents. The iso(thio)cyanates of the formula (III) are generally known compounds of organic chemistry.

Formula (IV) provides a general definition of the (thio)carbamoyl chlorides required as starting materials for carrying out process (b) according to the invention. In this formula (IV), R⁵, R⁶ and X preferably represent those radicals which have already been mentioned in connection with the description of the substances of the formula (I) according to the invention as being preferred for these substituents.

The (thio)carbamoyl chlorides of the formula (IV) are generally known or can be obtained with the aid of known processes (cf., for example, JP 57-108,057 or Chem. Abstr. 98: 53440y; JP-A 50-089,344 or Chem. Abstr. 83: 205987n; DE-A 2,429,523; AU-A 491,880 or Chem. Abstr. 89: 163572q).

The present invention also relates to certain related compounds of the general formula (XI)

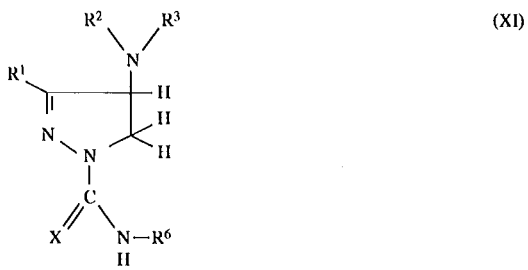

in which X R¹, R², R³ and R⁶ can in each case assume the following combinations of meanings:

TABLE I

| R¹ | R² | R³ | R⁶ | X |
|---|---|---|---|---|
| ⌬–Cl | Cl<br>⌬<br>–C–<br>‖<br>O | H | ⌬–CF₃ | O |

TABLE I-continued

| R¹ | R² | R³ | R⁶ | X |
|---|---|---|---|---|
| 4-F-phenyl | 2-Cl-benzoyl | H | 4-SCF₃-phenyl | O |
| 4-F-phenyl | 2-Cl-benzoyl | H | 4-OCHF₂-phenyl | O |
| 4-F-phenyl | 2-Cl-benzoyl | H | 3-CF₃-phenyl | O |
| 4-F-phenyl | 2-Cl-benzoyl | H | 3-Cl-phenyl | O |
| 4-Br-phenyl | 2-Cl-benzoyl | H | 4-CF₃-phenyl | O |
| 4-Br-phenyl | 2-Cl-benzoyl | H | 4-F-phenyl | O |
| 4-F-phenyl | 2-Cl-benzoyl | H | 4-Br-phenyl | O |
| 4-Br-phenyl | 2-Cl-benzoyl | H | 3-CF₃-phenyl | O |
| 4-Br-phenyl | 2-Cl-benzoyl | H | 4-Br-phenyl | O |
| 4-F-phenyl | 4-Br-benzoyl | H | 4-CF₃-phenyl | O |
| 4-F-phenyl | 4-F-benzoyl | H | 4-SCF₃-phenyl | O |

TABLE I-continued
| R¹ | R² | R³ | R⁶ | X |
|---|---|---|---|---|
|  | 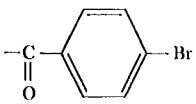 | H |  | O |
| 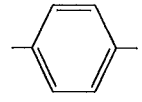 | 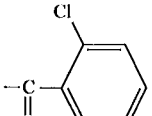 | H | 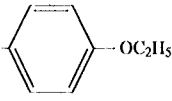OC₂H₅ | O |
| 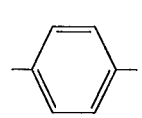 | 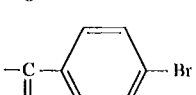 | H |  | O |
| 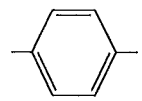 | 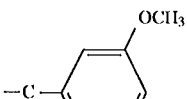 | H | 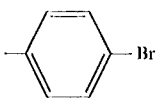 | O |
| 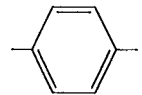 | 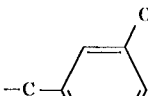 | H |  | O |
| 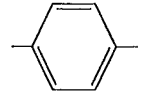 | 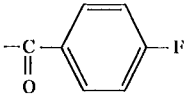 | H | 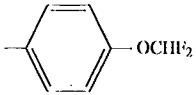OCHF₂ | O |
| 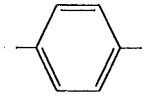 | 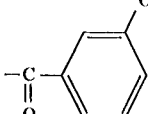 | H | OCF₃ | O |
| 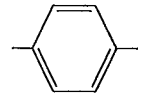 | 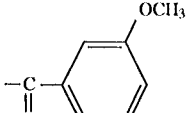 | H | CF₃ | O |
| 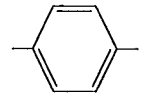 | 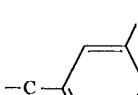 | H | 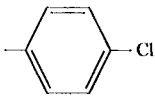 | O |
|  | 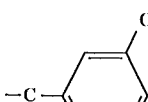 | H | 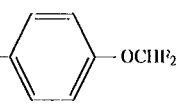OCHF₂ | O |
|  | 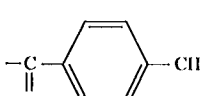 | H | 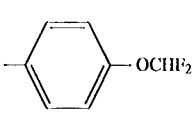OCHF₂ | O |

TABLE I-continued

| R¹ | R² | R³ | R⁶ | X |
|---|---|---|---|---|
| 4-Cl-C₆H₄ | 2-Cl-C₆H₄-C(=O)- | H | 4-F-C₆H₄ | O |
| 4-Cl-C₆H₄ | 2-Cl-C₆H₄-C(=O)- | H | 4-OCF₃-C₆H₄ | O |
| 4-Cl-C₆H₄ | 2-Cl-C₆H₄-C(=O)- | H | 4-Cl-C₆H₄ | O |
| 4-Cl-C₆H₄ | 2-Cl-C₆H₄-C(=O)- | H | 4-Br-C₆H₄ | O |
| 4-Cl-C₆H₄ | 2-Cl-C₆H₄-C(=O)- | H | 4-OCHF₂-C₆H₄ | O |
| 4-F-C₆H₄ | 4-F-C₆H₄-C(=O)- | H | 4-F-C₆H₄ | O |
| 4-F-C₆H₄ | 4-F-C₆H₄-C(=O)- | H | 4-OCF₃-C₆H₄ | O |
| 4-F-C₆H₄ | 4-F-C₆H₄-C(=O)- | H | 4-CF₃-C₆H₄ | O |
| 4-F-C₆H₄ | 4-F-C₆H₄-C(=O)- | H | 4-Cl-C₆H₄ | O |
| 4-F-C₆H₄ | 4-F-C₆H₄-C(=O)- | H | 4-Br-C₆H₄ | O |
| 4-F-C₆H₄ | 4-F-C₆H₄-C(=O)- | H | 4-OCHF₂-C₆H₄ | O |
| C₆H₅ | 4-Br-C₆H₄-C(=O)- | H | 4-CF₃-C₆H₄ | O |

TABLE I-continued
| R¹ | R² | R³ | R⁶ | X |
|---|---|---|---|---|
| 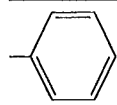 | 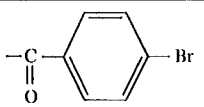 -C(=O)-C₆H₄-Br | H | 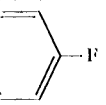 -C₆H₄-F | O |
| 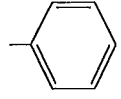 | 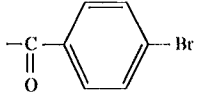 -C(=O)-C₆H₄-Br | H | 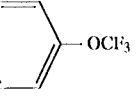 -C₆H₄-OCF₃ | O |
| 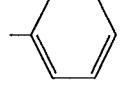 | 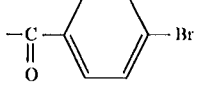 -C(=O)-C₆H₄-Br | H | 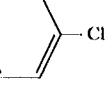 -C₆H₄-Cl | O |
| 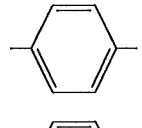 -C₆H₄-F | 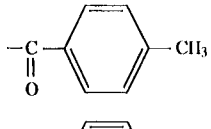 -C(=O)-C₆H₄-CH₃ | H | 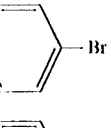 -C₆H₄-Br | O |
| 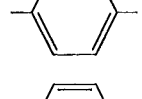 -C₆H₄-F | 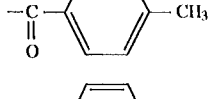 -C(=O)-C₆H₄-CH₃ | H | 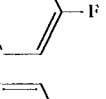 -C₆H₄-F | O |
|  -C₆H₄-F | 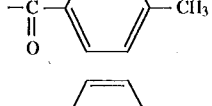 -C(=O)-C₆H₄-CH₃ | H | 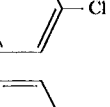 -C₆H₄-Cl | O |
|  -C₆H₄-F | 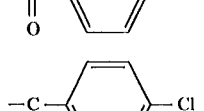 -C(=O)-C₆H₄-CH₃ | H | 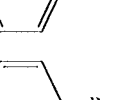 -C₆H₄-CF₃ | O |
| 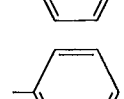 -C₆H₄-Cl | 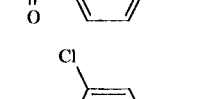 -C(=O)-C₆H₄-Cl | H | 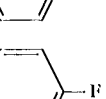 -C₆H₄-Br | O |
| 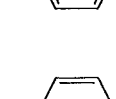 | 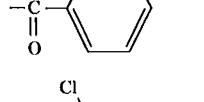 -C(=O)-C₆H₄(2-Cl) | H | 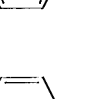 -C₆H₄-F | O |
| 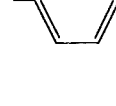 | 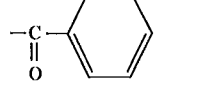 -C(=O)-C₆H₄(2-Cl) | H | 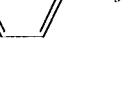 -C₆H₄-CF₃ | O |
| 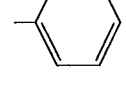 |  -C(=O)-C₆H₄(2-Cl) | H | 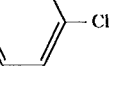 -C₆H₄-Cl | O |
| 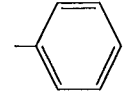 | 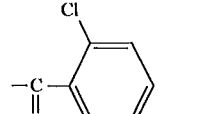 -C(=O)-C₆H₄(2-Cl) | H | 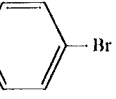 -C₆H₄-Br | O |
| 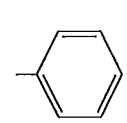 | 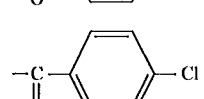 -C(=O)-C₆H₄-Cl | H | 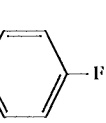 -C₆H₄-F | O |

TABLE I-continued

| R¹ | R² | R³ | R⁶ | X |
|---|---|---|---|---|
| 4-Cl-C₆H₄ | -C(O)-C₆H₅ | H | 4-Cl-C₆H₄ | O |
| 4-F-C₆H₄ | -C(O)-C₆H₄-4-Cl | H | 4-Br-C₆H₄ | O |
| 4-Cl-C₆H₄ | -C(O)-C₆H₅ | H | 4-Br-C₆H₄ | O |
| 4-Cl-C₆H₄ | -C(O)-C₆H₄-4-F | H | 4-Br-C₆H₄ | O |
| 4-Cl-C₆H₄ | -C(O)-C₆H₄-4-Cl | H | 4-Cl-C₆H₄ | O |
| 4-Br-C₆H₄ | -C(O)-C₆H₄-4-Br | H | 4-F-C₆H₄ | O |
| 4-Br-C₆H₄ | -C(O)-C₆H₄-4-Br | H | 4-OCF₃-C₆H₄ | O |
| 4-Br-C₆H₄ | -C(O)-C₆H₄-4-Br | H | 4-CF₃-C₆H₄ | O |
| 4-Br-C₆H₄ | -C(O)-C₆H₄-4-Br | H | 4-OCHF₂-C₆H₄ | O |
| 4-Br-C₆H₄ | -C(O)-C₆H₄-4-Br | H | 4-Cl-C₆H₄ | O |
| 4-Br-C₆H₄ | -C(O)-C₆H₄-4-Br | H | 4-Br-C₆H₄ | O |
| 4-Cl-C₆H₄ | -C(O)-C₆H₄-4-CH₃ | H | 4-Br-C₆H₄ | O |
| 4-Cl-C₆H₄ | -C(O)-C₆H₄-4-CH₃ | H | 4-Cl-C₆H₄ | O |
| 4-Cl-C₆H₄ | -C(O)-C₆H₅ | H | 4-CF₃-C₆H₄ | O |

TABLE I-continued

| R¹ | R² | R³ | R⁶ | X |
|---|---|---|---|---|
| 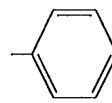 4-Cl-C₆H₄ | 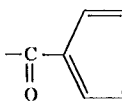 -C(O)-C₆H₅ | H | 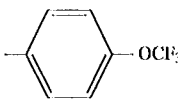 4-OCF₃-C₆H₄ | O |
| 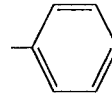 4-Cl-C₆H₄ | 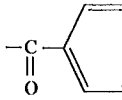 -C(O)-C₆H₅ | H | 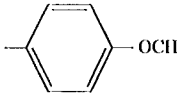 4-OCHF₂-C₆H₄ | O |
| 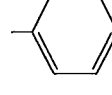 4-Br-C₆H₄ | 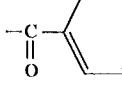 -C(O)-4-Cl-C₆H₄ | H | 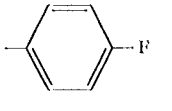 4-F-C₆H₄ | O |
| 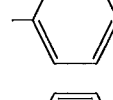 4-Br-C₆H₄ | 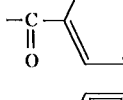 -C(O)-4-Cl-C₆H₄ | H | 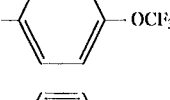 4-OCF₃-C₆H₄ | O |
| 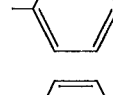 4-Br-C₆H₄ | 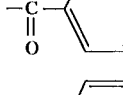 -C(O)-4-Cl-C₆H₄ | H | 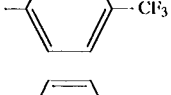 4-CF₃-C₆H₄ | O |
| 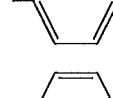 4-Br-C₆H₄ | 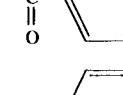 -C(O)-4-Cl-C₆H₄ | H |  4-Cl-C₆H₄ | O |
|  4-Br-C₆H₄ | 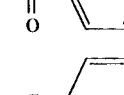 -C(O)-4-Cl-C₆H₄ | H | 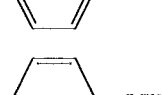 4-Br-C₆H₄ | O |
| 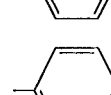 4-Br-C₆H₄ | 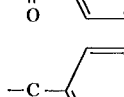 -C(O)-4-Cl-C₆H₄ | H | 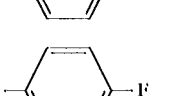 4-OCHF₂-C₆H₄ | O |
| 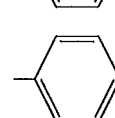 4-Br-C₆H₄ | 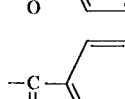 -C(O)-C₆H₅ | H | 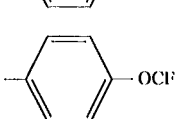 4-F-C₆H₄ | O |
| 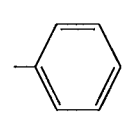 4-Br-C₆H₄ | 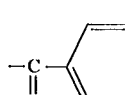 -C(O)-C₆H₅ | H |  4-OCF₃-C₆H₄ | O |
| 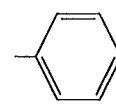 C₆H₅ | 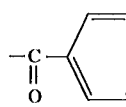 -C(O)-4-Br-C₆H₄ | H | 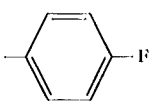 4-Br-C₆H₄ | O |
| 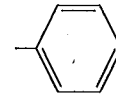 4-Cl-C₆H₄ | 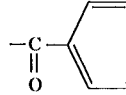 -C(O)-4-CH₃-C₆H₄ | H | 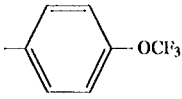 4-F-C₆H₄ | O |
| 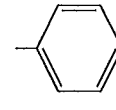 4-Cl-C₆H₄ | 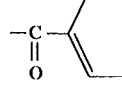 -C(O)-4-CH₃-C₆H₄ | H | 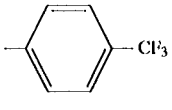 4-OCF₃-C₆H₄ | O |
|  4-Cl-C₆H₄ |  -C(O)-4-CH₃-C₆H₄ | H |  4-CF₃-C₆H₄ | O |

TABLE I-continued

| R¹ | R² | R³ | R⁶ | X |
|---|---|---|---|---|
| 4-Cl-C₆H₄ | 4-Cl-C₆H₄-C(O)- | H | 4-F-C₆H₄ | O |
| 4-Cl-C₆H₄ | 4-Cl-C₆H₄-C(O)- | H | 4-OCF₃-C₆H₄ | O |
| 4-Cl-C₆H₄ | 4-Cl-C₆H₄-C(O)- | H | 4-CF₃-C₆H₄ | O |
| 4-Cl-C₆H₄ | 4-Cl-C₆H₄-C(O)- | H | 4-OCHF₂-C₆H₄ | O |
| 4-Br-C₆H₄ | C₆H₅-C(O)- | H | 4-CF₃-C₆H₄ | O |
| 4-Br-C₆H₄ | C₆H₅-C(O)- | H | 4-Cl-C₆H₄ | O |
| 4-F-C₆H₄ | 4-CH₃-C₆H₄-C(O)- | H | 4-OCF₃-C₆H₄ | O |
| 4-F-C₆H₄ | 4-CH₃-C₆H₄-C(O)- | H | 4-OCHF₂-C₆H₄ | O |
| 4-Br-C₆H₄ | C₆H₅-C(O)- | H | 4-Br-C₆H₄ | O |
| 4-Br-C₆H₄ | C₆H₅-C(O)- | H | 4-OCF₃-C₆H₄ | O |
| 4-Cl-C₆H₄ | 4-F-C₆H₄-C(O)- | H | 4-F-C₆H₄ | O |
| 4-Cl-C₆H₄ | 4-F-C₆H₄-C(O)- | H | 4-OCF₃-C₆H₄ | O |
| 4-Cl-C₆H₄ | 4-F-C₆H₄-C(O)- | H | 4-CF₃-C₆H₄ | O |
| C₆H₅ | C₆H₅-C(O)- | H | 4-F-C₆H₄ | O |

TABLE I-continued

| R¹ | R² | R³ | R⁶ | X |
|---|---|---|---|---|
| phenyl | -C(=O)-phenyl | H | 4-Cl-phenyl | O |
| phenyl | -C(=O)-phenyl | H | 4-Br-phenyl | O |
| phenyl | -C(=O)-(4-F-phenyl) | H | 4-Cl-phenyl | O |
| phenyl | -C(=O)-(4-F-phenyl) | H | 4-Br-phenyl | O |
| phenyl | -C(=O)-(4-CH₃-phenyl) | H | 3-Cl-4-OCF₃-phenyl | O |
| phenyl | -C(=O)-(2-Cl-phenyl) | H | 4-OCF₃-phenyl | O |
| phenyl | -C(=O)-(2-Cl-phenyl) | H | 4-OCHF₂-phenyl | O |
| phenyl | -C(=O)-(4-F-phenyl) | H | 4-F-phenyl | O |
| 4-F-phenyl | -C(=O)-(4-CH₃-phenyl) | H | 4-CF₃-cyclohexyl | O |
| phenyl | -C(=O)-(2-CH₃O-phenyl) | H | 4-F-phenyl | O |
| phenyl | -C(=O)-(2-CH₃O-phenyl) | H | 4-OCF₃-phenyl | O |
| phenyl | -C(=O)-(2-CH₃O-phenyl) | H | 4-CF₃-phenyl | O |

TABLE I-continued

| R¹ | R² | R³ | R⁶ | X |
|---|---|---|---|---|
| phenyl | 2-CH₃O-benzoyl | H | 4-Cl-phenyl | O |
| phenyl | 2-CH₃O-benzoyl | H | 4-Br-phenyl | O |
| phenyl | 2-CH₃O-benzoyl | H | 4-OCHF₂-phenyl | O |
| 4-F-phenyl | 4-Cl-benzoyl | H | 4-F-phenyl | O |
| 4-F-phenyl | 4-Cl-benzoyl | H | 4-OCF₃-phenyl | O |
| 4-F-phenyl | 4-Cl-benzoyl | H | 4-CF₃-phenyl | O |
| 4-F-phenyl | 4-Cl-benzoyl | H | 4-Cl-phenyl | O |
| 4-F-phenyl | 4-Cl-benzoyl | H | 4-OCHF₂-phenyl | O |
| 4-Cl-phenyl | 4-F-benzoyl | H | 4-Cl-phenyl | O |
| 4-F-phenyl | 4-F-benzoyl | H | 3-Cl-phenyl | O |
| 4-F-phenyl | 4-F-benzoyl | H | 3-CF₃-phenyl | O |
| 4-F-phenyl | 4-Br-benzoyl | H | 4-Br-phenyl | O |

TABLE I-continued

| R¹ | R² | R³ | R⁶ | X |
|---|---|---|---|---|
| 4-F-C₆H₄- | -C(O)-C₆H₄-4-Br | H | 4-Cl-C₆H₄- | O |
| 4-Cl-C₆H₄- | -C(O)-C₆H₄-4-F | H | 3-CF₃-C₆H₄- | O |
| 4-Cl-C₆H₄- | -C(O)-C₆H₄-4-F | H | 2-CN-6-F-C₆H₃- | O |
| 4-Br-C₆H₄- | -C(O)-C₆H₄-4-F | H | 4-CF₃-C₆H₄- | O |
| 4-Br-C₆H₄- | -C(O)-C₆H₄-4-F | H | 4-F-C₆H₄- | O |
| 4-Br-C₆H₄- | -C(O)-C₆H₄-4-F | H | 3-CF₃-C₆H₄- | O |
| 4-Br-C₆H₄- | -C(O)-C₆H₄-4-F | H | 4-Br-C₆H₄- | O |
| 4-Br-C₆H₄- | -C(O)-C₆H₄-4-F | H | 4-Cl-C₆H₄- | O |
| 4-Cl-C₆H₄- | -C(O)-C₆H₄-2-Cl | H | 4-Cl-C₆H₄- | O |
| 4-Cl-C₆H₄- | -C(O)-C₆H₄-4-CH₃ | H | 3-CF₃-C₆H₄- | O |
| 4-Cl-C₆H₄- | -C(O)-C₆H₄-2-Cl | H | 3-CF₃-C₆H₄- | O |
| 4-F-C₆H₄- | -C(O)-C₆H₄-4-Cl | H | 3-CF₃-C₆H₄- | O |

TABLE I-continued

| R¹ | R² | R³ | R⁶ | X |
|---|---|---|---|---|
| 4-Cl-C₆H₄- | -C(O)-C₆H₄-4-F | H | 3-Cl-C₆H₄- | O |
| 4-Br-C₆H₄- | -C(O)-(CH₂)₅- | | 4-CF₃-C₆H₄- | O |
| 4-Br-C₆H₄- | -C(O)-(CH₂)₅- | | 4-F-C₆H₄- | O |
| 4-Br-C₆H₄- | -C(O)-(CH₂)₅- | | 4-OCF₃-C₆H₄- | O |
| 4-Br-C₆H₄- | -C(O)-(CH₂)₅- | | 4-Cl-C₆H₄- | O |
| 4-Br-C₆H₄- | -C(O)-(CH₂)₅- | | 4-Br-C₆H₄- | O |
| 4-Br-C₆H₄- | -C(O)-(CH₂)₅- | | 4-OCHF₂-C₆H₄- | O |
| 4-Br-C₆H₄- | -C(O)-(CH₂)₅- | | 4-CF₃-C₆H₄- | O |
| 4-Cl-C₆H₄- | -C(O)-CH₂-CH(CH₃)₂ | H | 4-OCF₃-C₆H₄- | O |
| 4-Cl-C₆H₄- | -C(O)-CH₂-CH(CH₃)₂ | H | 4-CF₃-C₆H₄- | O |
| 4-Cl-C₆H₄- | -C(O)-CH₂-CH(CH₃)₂ | H | 4-Cl-C₆H₄- | O |
| 4-Cl-C₆H₄- | -C(O)-CH₂-CH(CH₃)₂ | H | 4-F-C₆H₄- | O |
| 4-Cl-C₆H₄- | -C(O)-CH₂-CH(CH₃)₂ | H | 4-Br-C₆H₄- | O |
| 4-Cl-C₆H₄- | -C(O)-CH₂-CH(CH₃)₂ | H | 4-O-CHF₂-C₆H₄- | O |

TABLE I-continued

| R¹ | R² | R³ | R⁶ | X |
|---|---|---|---|---|
| 4-Cl-C₆H₄- | -C(=O)-CH₃ | H | 4-F-C₆H₄- | O |
| 4-Cl-C₆H₄- | -C(=O)-CH₂-CH₃ | H | 4-OCF₃-C₆H₄- | O |
| 4-Cl-C₆H₄- | -C(=O)-CH₂-CH₃ | H | 4-Cl-C₆H₄- | O |
| 4-Cl-C₆H₄- | -C(=O)-CH₂-CH₃ | H | 4-Br-C₆H₄- | O |
| 4-F-C₆H₄- | -C(=O)-OCH₃ | H | 4-Br-C₆H₄- | O |
| 4-F-C₆H₄- | -C(=O)-CH₂-CH(CH₃)₂ | H | 4-F-C₆H₄- | O |
| 4-Br-C₆H₄- | -C(=O)-(CH₂)₃- | | 4-CF₃-C₆H₄- | O |
| 4-Cl-C₆H₄- | -C(=O)-CH₂-CH(CH₃)₂ | H | 4-CF₃-C₆H₄- | O |
| 4-Cl-C₆H₄- | -C(=O)-CH(CH₃)₂ | H | 4-CF₃-C₆H₄- | O |
| 4-F-C₆H₄- | -C(=O)-CH₂-CH(CH₃)₂ | H | 4-OCF₃-C₆H₄- | O |
| 4-F-C₆H₄- | -C(=O)-CH₂-CH(CH₃)₂ | H | 4-Br-C₆H₄- | O |
| 4-F-C₆H₄- | -C(=O)-CH₂-CH(CH₃)₂ | H | 4-O-CHF₂-C₆H₄- | O |
| 4-F-C₆H₄- | -C(=O)-CH₂-CH(CH₃)₂ | H | 4-O-CF₃-C₆H₄- | O |
| 4-Cl-C₆H₄- | -C(=O)-CH(CH₃)₂ | H | 4-O-CF₃-C₆H₄- | O |

TABLE I-continued

| R¹ | R² | R³ | R⁶ | X |
|---|---|---|---|---|
| 4-Cl-C₆H₄- | -C(O)-CH(CH₃)₂ | H | 4-CF₃-C₆H₄- | O |
| 4-Cl-C₆H₄- | -C(O)-CH(CH₃)₂ | H | 4-F-C₆H₄- | O |
| 4-Cl-C₆H₄- | -C(O)-CH(CH₃)₂ | H | 4-Cl-C₆H₄- | O |
| 4-Cl-C₆H₄- | -C(O)-CH(CH₃)₂ | H | 4-Br-C₆H₄- | O |
| 4-Cl-C₆H₄- | -C(O)-CH(CH₃)₂ | H | 4-(O-CHF)-C₆H₄- | O |
| 4-Cl-C₆H₄- | -C(O)-CH(CH₃)₂ | H | 4-(S-CF₃)-C₆H₄- | O |
| 4-Cl-C₆H₄- | -C(O)-CH(CH₃)₂ | H | 3-Cl-C₆H₄- | O |
| 4-Cl-C₆H₄- | -C(O)-CH(CH₃)₂ | H | 4-Cl-C₆H₄- | O |
| 4-Br-C₆H₄- | -C(O)-(CH₂)₃- | | 4-F-C₆H₄- | O |
| 4-Br-C₆H₄- | -C(O)-(CH₂)₃- | | 4-(O-CF₃)-C₆H₄- | O |
| 4-Br-C₆H₄- | -C(O)-(CH₂)₃- | | 4-Cl-C₆H₄- | O |
| 4-Br-C₆H₄- | -C(O)-CH₃ | H | 4-CF₃-C₆H₄- | O |
| 4-Br-C₆H₄- | -C(O)-CH₃ | H | 4-Cl-C₆H₄- | O |
| 4-Br-C₆H₄- | -C(O)-OCH₃ | H | 4-(O-CF₃)-C₆H₄- | O |

TABLE I-continued
| R¹ | R² | R³ | R⁶ | X |
|---|---|---|---|---|
| 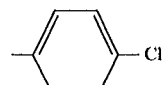 | 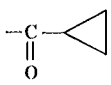 | H | 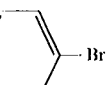 | O |
| 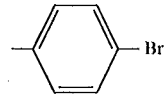 | 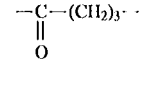 | | 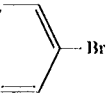 | O |
| 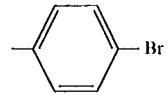 | 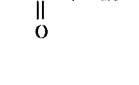 | | 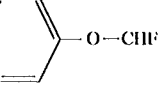 | O |
| 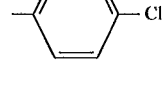 | 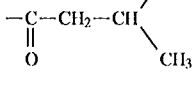 | H | 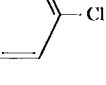 | O |
|  | 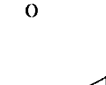 | H | 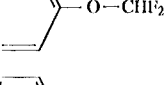 | O |
|  | 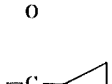 | H | 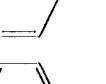 | O |
| 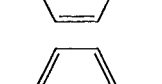 | 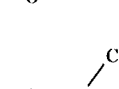 | H | 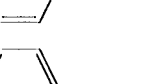 | O |
| 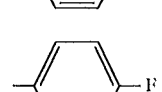 | 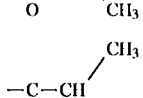 | H | 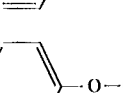 | O |
| 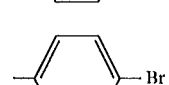 | 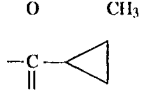 | H | 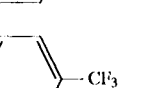 | O |
| 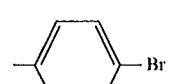 | 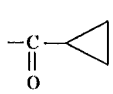 | H | 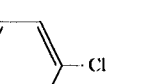 | O |
|  | 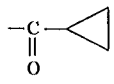 | H | 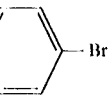 | O |
|  | 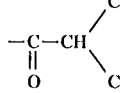 | H | 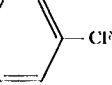 | O |
|  | 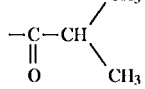 | H | 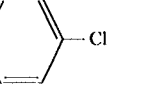 | O |
|  |  | H |  | O |

TABLE I-continued

| R¹ | R² | R³ | R⁶ | X |
|---|---|---|---|---|
| 4-F-C₆H₄- | -C(O)-CH(CH₃)₂ | H | 4-(OCHF₂)-C₆H₄- | O |
| 4-Cl-C₆H₄- | -C(O)-CH(CH₃)₂ | H | 4-Cl-C₆H₄- | S |
| 4-Cl-C₆H₄- | -C(O)-CH(CH₃)₂ | H | 4-Br-C₆H₄- | S |

Furthermore, it has been found that the new substituted pyrazolines of the general formula (XI)

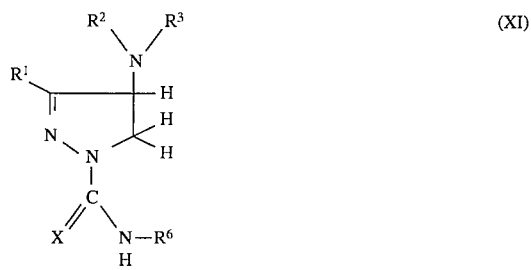

in which the substituents X, R¹, R², R³ and R⁶ have the meaning in Table I are obtained when pyrazolines of the formula (II) which are unsubstituted in the 1-position,

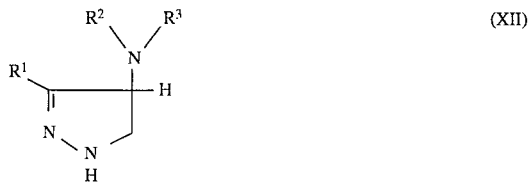

in which
R¹, R² and R³ have the meaning in Table I are reacted either
a) with isocyanates of the formula (XIII)

$$R_6-N=C=X \quad (XIII)$$

in which
R⁶ have the meaning in Table I, or
b) with carbamoyl chlorides of the formula (XIV)

in which
R⁶ has the meaning in Table I, if appropriate in the presence of a diluent and if appropriate in the presence of a reaction auxiliary.

Finally, it has been found that the new substituted pyrazolines of the general formula (XI) have a good activity against animal pests.

Surprisingly, the substituted pyrazolines of the general formula (XI) according to the invention have a considerably better insecticidal activity compared with compounds which are known from the prior art and related chemically and/or from the point of view of their action.

Specific reference may be made to the compounds mentioned in the preparation examples.

If, for example, 3-(4-chlorophenyl)-4-[(2-chlorophenyl)carbonylamino]-4,5-dihydropyrazole and 4-trifluoromethylphenyl isocyanate are used as starting material, the course of the reaction of process (c) according to the invention can be represented by the following equation:

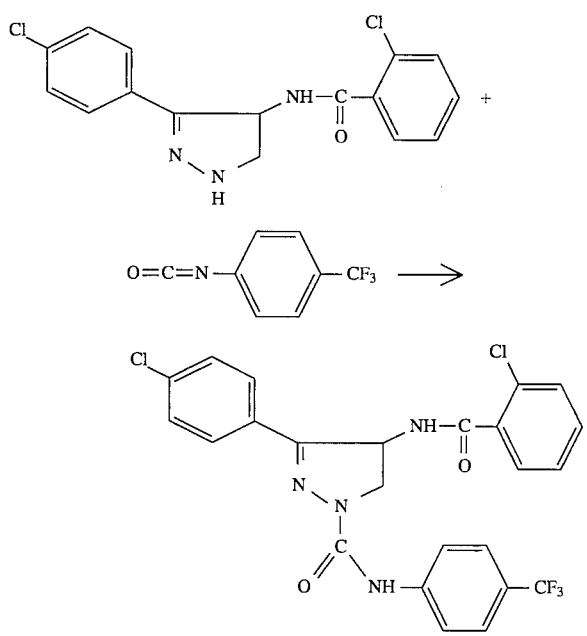

If, for example, 3-(4-chlorophenyl)-4-[(2-chlorophenyl)carbonylamino]-4,5-dihydropyrazole and N-methyl-N-(4-trifluoromethylphenyl)-carbamoyl chloride are used as starting materials, the course of the reaction of process (d) according to the invention can be represented by the following equation:

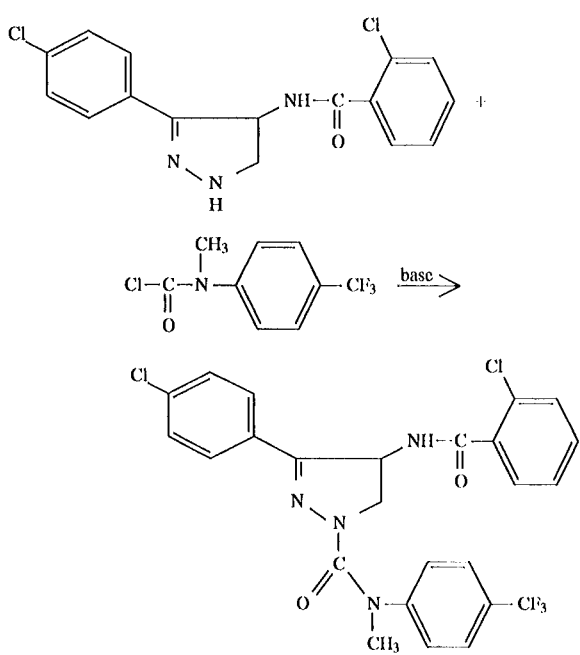

Formula (XII) provides a general definition of the pyrazolines which are unsubstituted in the 1-position and which are required as starting materials for carrying out process (c) and (d) according to the invention. In this formula (XII), $R^1$, $R^2$ and $R^3$ represent those radicals which have already been mentioned in connection with the description of the compounds of the formula (XI) according to the invention.

The pyrazolines of the formula (XII) which are unsubstituted in the 1-position are not yet known. They are obtained, for example, when phenacylamine derivatives of the formula (XV)

in which
$R^1$, $R^2$ and $R^3$ have the meaning in Table I are reacted with dimethylmethyleneimmonium chloride of the formula (XVI)

if appropriate in the presence of a diluent such as, for example, acetonitrile, at temperatures between 30° C. and 80° C. and, in a subsequent 2nd step, the resulting phenacyldiamine derivatives of the formula (XVII)

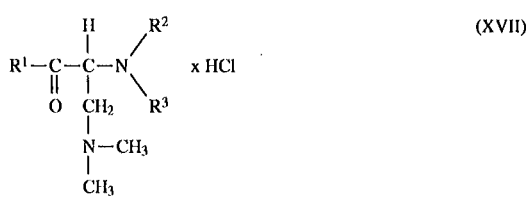

in which
$R^1$, $R^2$ and $R^3$ have the meaning in Table I, are reacted with hydrazine hydrate, if appropriate in the presence of a diluent such as, for example, acetonitrile, at temperatures between 30° C. and 80° C.

In this context, it is also possible and may be advantageous to carry out the reaction of the phenacylamine derivatives of the formula (XV) with dimethylmethyleneimmonium chloride of the formula (XVI) and the subsequent reaction of the resulting phenacyldiamine derivatives of the formula (XVII) with hydrazine hydrate in one reaction step in a so-called "one-pot process".

Alternatively, the pyrazolines of the formula (XII) are also obtained when phenacylamine derivatives of the formula (XVa)

in which
$R^1$, $R^2$ and $R^3$ have the meaning in Table I, are initially reacted, in a first step, with formaldehyde at temperatures between 30° C. and 80° C., if appropriate in the presence of a diluent such as, for example, ethanol, and the resulting phenacyl-enamine derivatives of the formula (XVIII)

in which
$R^1$, $R^2$ and $R^3$ have the abovementioned meaning, are subsequently reacted with hydrazine hydrate at temperatures between 30° C. and 80° C., if appropriate in the presence of a diluent such as, for example, ethanol.

In this context, it is also possible and may be advantageous to carry out the reaction of the phenacylamine derivatives of the formula (XVa) with formaldehyde and the subsequent reaction of the resulting phenacyl-enamine derivatives of the formula (XVIII) with hydrazine hydrate in one reaction step, in a so-called "one-pot process".

Phenacylamine derivatives of the formulae (XV) or (XVa) are known or can be obtained analogously to known processes (cf., for example, Chem. Ber. 122, 295–300 [1989]; J. Med. Chem. 29, 333–341 [1986]; J. Amer. Chem. Soc. 98, 3621–3627 [1976]; Tetrahedron 31, 2145–2149 [1975]; Zh. Org. Khim. 10, 2429–2436 [1974]; J. Org. Chem. 55, 3658–3660 [1990]; Chem. Ind. 1975, 177; Synthesis 1990, 520).

Dimethylmethyleneimmonium chloride of the formula (XVI) is known (cf., for example, J. Org. Chem. 47, 2940–2944 [1982]; Bull. Soc. Chim. Fr. 1970, 2707–2711).

Some of the phenacyldiamine derivatives of the formula (XVII) are known (cf., for example, U.S. Pat. No. 2,980,674 [1957] and CA 56: 3419 [1962]).

Phenacyl-enamine derivatives of the formula (XVIII) are known or can be obtained analogously to known processes (cf., for example, Chem. Ber. 93, 387–391 [1960]; Sankyo Kenkyusho Nempo 15, 36 [1963] and Chem. Abstr. 60: 11876d [1964]; J. Med. Chem. 30, 1497–1502 [1987]; JP 61-053,239; U.S. Pat. No. 4,277,420; Chem. Abstr. 87: 67928y; Khim.-Farm. Zh. 9, 21–24 [1975] and CA 83: 58351v; Collect. Czech. Commun. 19, 317–328 [1954]; Ann. Chim. 46, 267–269 [1956]; J. Chem. Soc. 1953, 4066–4073; Zh. Obshch. Khim. 30, 3714 [1960]; Pharm. Chem. J. 9, 301–304 [1975]).

Formula (XIII) provides a general definition of the isocyanates required as starting materials for carrying out process (c) according to the invention. In this formula (XIII), $R^6$ preferably represents those radicals which have already been mentioned in connection with the description of the compounds of the formula (XI) according to the invention.

The isocyanates of the formula (XIII) are generally known compounds of organic chemistry.

Formula (XIV) provides a general definition of the carbamoyl chlorides required as starting materials for carrying out process (d) according to the invention. In this formula (XIV), $R^6$ represents those radicals which have already been mentioned for these substituents in connection with the description of the substances of the formula (XI) according to the invention.

The carbamoyl chlorides of the formula (XIV) are generally known or can be obtained with the aid of known processes (cf., for example, JP 57-108,057 and Chem. Abstr. 98; 53440y; JP-A 50-089,344 and Chem. Abstr. 83: 205987n; DE-A 2,429,523; AU-A 491,880 and Chem. Abstr. 89; 163572q).

Suitable diluents for carrying out processes (a), (b), (c) and (d) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles such as acetonitrile, propionitrile or benzonitrile; amides such as N,N-dimethylformamide, N,Ndimethylacetamide, N-methylformanilide, N-methylpyrrolidone or hexamethylphosphoric triamide, esters such as methyl acetate or ethyl acetate, or sulphoxides such as dimethyl sulphoxide.

Processes (a), (b), (c), and (d) according to the invention can preferably be carried out in the presence of a suitable reaction auxiliary. Suitable reaction auxiliaries are all customary inorganic or organic bases. These include, for example, alkaline earth metal hydroxides or alkali metal hydroxides such as sodium hydroxide, calcium hydroxide, potassium hydroxide or else ammonium hydroxide, alkali metal carbonates such as sodium carbonate, potassium carbonate, potassium hydrogen carbonate, sodium hydrogen carbonate or ammonium carbonate, alkali metal acetates or alkaline earth metal acetates such as sodium acetate, potassium acetate, calcium acetate or ammonium acetate, and also tertiary amines such as trimethylamine, triethylamine, tributylamlne, N,N-dimethylaniline, pyridine, piperidine, N-methylpiperidine, N,N-dimethylaminopyridine, diazabicyclooctane (DABC0), diazabicyclononene (DBN) or diazabicycloundecene (DBU).

When carrying out processes (a), (b), (c), and (d) according to the invention, the reaction temperatures can be varied within a substantial range. In general, the process is carried out at temperatures between 0° C. and 120° C., preferably at temperatures between 20° C. and 80° C.

Processes (a), (b), (c), and (d) according to the invention are customarily carried out under atmospheric pressure. However, it is also possible to carry out the processes under increased or reduced pressure.

For carrying out process (c) according to the invention, 1.0 to 2.5 moles, preferably 1.0 to 1.5 moles, of isocyanate of the formula (XIII) and, if appropriate, 0.01 to 2.0 moles, preferably 0.1 to 1.2 moles, of base used as a reaction auxiliary are generally employed per mole of pyrazoline of the formula (XII) which is unsubstituted in the 1-position. The reaction is carried out and the reaction products are worked up and isolated by generally customary methods (cf. in this context the Preparation Examples).

For carrying out process (d) according to the invention, 1.0 to 2.5 moles, preferably 1.0 to 1.5 moles, of carbamoyl chloride of the formula (XIV) and, if appropriate, 0.01 to 2.0 moles, preferably 0.1 to 1.2 moles, of base used as reaction auxiliary are generally employed per mole of pyrazoline of the formula (XII) which IS unsubstituted in the 1-position. The reaction is carried out and the reaction products are worked up and isolated by generally customary methods.

The active compounds are suitable for controlling animal pests, preferably arthropodes and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and *Scutigera spec;* from the order of the Symphyla, for example, *Scutigerella immaculata;* from the order of the Thysanura, for example, *Lepisma saccharina;* from the order of the Collembola, for example, *Onychiurus armatus;* from the order of the Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example, *Forficula auricularia;* from the order of the Isoptera, for example, *Reticulitermes* spp.;

from the order of the Anoplura, for example, *Phylloxera vastatrix, Pemphigus* spp., *Pediculus humanus corporis, Haematopinus* spp. and *Linognathus* spp;

from the order of the Mallophaga, for example, *Trichodectes* spp. and *Damalinea* spp.;

from the order of the Thysanoptera, for example, *Hercinothrips femoralis* and *Thrips tabaci;* from the order of the Heteroptera, for example, *Eurygaster* spp., *Dysdercus intermedius, Piesma quadrata, Cimex lectularius, Rhodnius prolixus* and *Triatoma* spp.;

from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. *Psylla* spp.;

from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp. *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kue-*

*hniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varive stis, Atomaria* spp., *Oryzaephilus surinamensis, Aritho nomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Cono derus* spp., *Melolontha melolontha, Amphimallon solsti tialis* and *Costelytra zealandica;* from the order of the Hymenoptera, for example, *Diprion* spp., *Hoplocampa* spp., *Lasius* spp., *Monomorium pharaonis* and *Vespa* spp.;

from the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the Siphonaptera, for example, *Xenopsylla cheopis* and *Ceratophyllus* spp.

From the order of the Arachnida, for example, *Scorpio maurus* and *Latrodectus mactans;* from the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The phytoparasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp. and *Trichodorus* spp.

In this context, the active compounds can be employed with particularly good success for combatting insects which are harmful to plants such as, for example, against the larvae of the mustard beetles (*Phaedon cochleariae*) or against the caterpillars of the cabbage moth (*Plutella maculipennis*).

Depending on their particular physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can exist in their commercially available formulations and in the use forms prepared from these formulations in the form of a mixture with other active compounds such as insecticides, attractants, sterilants, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The active compounds can furthermore exist in their commercially available formulations and in the use forms prepared from these formulations in the form of a mixture with synergistics. Synergistics are compounds by which the action of the active compounds is increased without it being necessary for the synergistic added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

They are used in a customary manner adapted to suit one of these forms.

When used against hygiene pests and stored-product pests, the active compounds are distinguished by an outstanding residual action on wood and clay and by a good stability to alkali on limed substrates.

The preparation and use of the active compounds according to the invention can be seen from the examples which follow:

PREPARATION EXAMPLES FOR COMPOUNDS OF FORMULA (XI)

EXAMPLE 1

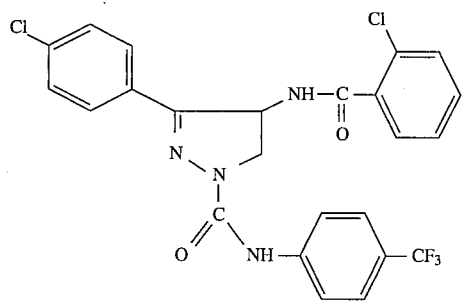

(Process (c))

1.2 g (0.00642 mol) of 4-trifluoromethylphenyl isocyanate are added dropwise with stirring at room temperature to 2 g (0.00598 mol) of 3-(4-chlorophenyl)-4-[(2-chlorophenyl)-carbonylamino]-4,5-dihydropyrazole in 50 ml of dichloromethane, and the mixture is refluxed for one hour.

For working-up, the reaction mixture is cooled, and solid which has precipitated is filtered off with suction and dried.

1.6 g (51% of theory) of 3-(4-chlorophenyl)-4-[(2-chlorophenyl)-aminocarbonyl]-1-[(4-trifluoromethylphenyl)-aminocarbonyl] -4,5-dihydropyrazole of melting point >200° C. are obtained.

$^1$H-NMR (DMSO-$d_6$/tetramethylsilane): δ=3.96(dd); 4.29(t); 5.95(m); 9.33(d); 9.53(s) ppm.

The following substituted pyrazolines of the general formula (XI) are obtained in an analogous manner and following the general preparation instructions:

| Ex. | R$^1$ | R$^2$ | R$^3$ | R$^6$ |
|---|---|---|---|---|
| 2 | —⟨C$_6$H$_4$⟩—F | —C(=O)—⟨2-Cl-C$_6$H$_4$⟩ | H | —⟨C$_6$H$_4$⟩—SCF$_3$ |
| 3 | —⟨C$_6$H$_4$⟩—F | —C(=O)—⟨2-Cl-C$_6$H$_4$⟩ | H | —⟨C$_6$H$_4$⟩—OCHF$_2$ |
| 4 | —⟨C$_6$H$_4$⟩—F | —C(=O)—⟨2-Cl-C$_6$H$_4$⟩ | H | —⟨C$_6$H$_4$⟩—CF$_3$ |
| 5 | —⟨C$_6$H$_4$⟩—F | —C(=O)—⟨2-Cl-C$_6$H$_4$⟩ | H | —⟨C$_6$H$_4$⟩—Cl |

-continued (XI) structure: pyrazoline ring with R¹ at C3, R²R³N- at C4 (with H), CH₂ (H,H) at C5, N1-C(=O)-NH-R⁶

| Ex. | R¹ | R² | R³ | R⁶ |
|---|---|---|---|---|
| 6 | 4-Br-C₆H₄- | 2-Cl-C₆H₄-C(=O)- | H | 4-CF₃-C₆H₄- |
| 7 | 4-Br-C₆H₄- | 2-Cl-C₆H₄-C(=O)- | H | 4-F-C₆H₄- |
| 8 | 4-F-C₆H₄- | 2-Cl-C₆H₄-C(=O)- | H | 4-Br-C₆H₄- |
| 9 | 4-Br-C₆H₄- | 2-Cl-C₆H₄-C(=O)- | H | 3-CF₃-C₆H₄- |
| 10 | 4-Br-C₆H₄- | 2-Cl-C₆H₄-C(=O)- | H | 4-Br-C₆H₄- |
| 11 | 4-F-C₆H₄- | 4-Br-C₆H₄-C(=O)- | H | 4-CF₃-C₆H₄- |
| 12 | 4-F-C₆H₄- | 4-F-C₆H₄-C(=O)- | H | 4-SCF₃-C₆H₄- |
| 13 | 4-F-C₆H₄- | 4-Br-C₆H₄-C(=O)- | H | 4-F-C₆H₄- |
| 14 | 4-F-C₆H₄- | 2-Cl-C₆H₄-C(=O)- | H | 4-OC₂H₅-C₆H₄- |
| 15 | 4-F-C₆H₄- | 4-Br-C₆H₄-C(=O)- | H | 3-CF₃-C₆H₄- |

-continued $$\text{(XI)}$$

| Ex. | R¹ | R² | R³ | R⁶ |
|---|---|---|---|---|
| 16 | 4-Cl-C₆H₄ | 3-OCH₃-C₆H₄-C(=O)- | H | 4-Br-C₆H₄ |
| 17 | 4-Cl-C₆H₄ | 3-OCH₃-C₆H₄-C(=O)- | H | 4-F-C₆H₄ |
| 18 | 4-Cl-C₆H₄ | 4-F-C₆H₄-C(=O)- | H | 4-OCHF₂-C₆H₄ |
| 19 | 4-Cl-C₆H₄ | 3-OCH₃-C₆H₄-C(=O)- | H | 4-OCF₃-C₆H₄ |
| 20 | 4-Cl-C₆H₄ | 3-OCH₃-C₆H₄-C(=O)- | H | 4-CF₃-C₆H₄ |
| 21 | 4-Cl-C₆H₄ | 3-OCH₃-C₆H₄-C(=O)- | H | 4-Cl-C₆H₄ |
| 22 | 4-Cl-C₆H₄ | 3-OCH₃-C₆H₄-C(=O)- | H | 4-OCHF₂-C₆H₄ |
| 23 | 4-Cl-C₆H₄ | 3-OCH₃-C₆H₄-C(=O)- | H | 4-CF₃-C₆H₁₀ |
| 24 | 4-Cl-C₆H₄ | 4-CH₃-C₆H₄-C(=O)- | H | 4-OCHF₂-C₆H₄ |

-continued
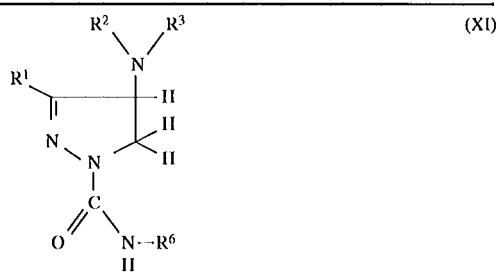
(XI)
| Ex. | R¹ | R² | R³ | R⁶ |
|---|---|---|---|---|
| 25 | 4-Cl-C₆H₄ | 2-Cl-C₆H₄-C(=O)- | H | 4-F-C₆H₄ |
| 26 | 4-Cl-C₆H₄ | 2-Cl-C₆H₄-C(=O)- | H | 4-OCF₃-C₆H₄ |
| 27 | 4-Cl-C₆H₄ | 2-Cl-C₆H₄-C(=O)- | H | 4-Cl-C₆H₄ |
| 28 | 4-Cl-C₆H₄ | 2-Cl-C₆H₄-C(=O)- | H | 4-Br-C₆H₄ |
| 29 | 4-Cl-C₆H₄ | 2-Cl-C₆H₄-C(=O)- | H | 4-OCHF₂-C₆H₄ |
| 30 | 4-F-C₆H₄ | 4-F-C₆H₄-C(=O)- | H | 4-F-C₆H₄ |
| 31 | 4-F-C₆H₄ | 4-F-C₆H₄-C(=O)- | H | 4-OCF₃-C₆H₄ |
| 32 | 4-F-C₆H₄ | 4-F-C₆H₄-C(=O)- | H | 4-CF₃-C₆H₄ |
| 33 | 4-F-C₆H₄ | 4-F-C₆H₄-C(=O)- | H | 4-Cl-C₆H₄ |
| 34 | 4-F-C₆H₄ | 4-F-C₆H₄-C(=O)- | H | 4-Br-C₆H₄ |

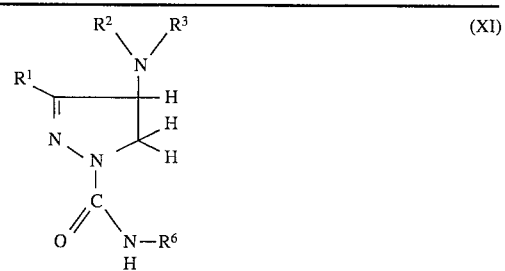
| Ex. | R¹ | R² | R³ | R⁶ |
|---|---|---|---|---|
| 35 | 4-F-C₆H₄ | -C(O)-C₆H₄-4-F | H | 4-OCHF₂-C₆H₄ |
| 36 | C₆H₅ | -C(O)-C₆H₄-4-Br | H | 4-CF₃-C₆H₄ |
| 37 | C₆H₅ | -C(O)-C₆H₄-4-Br | H | 4-F-C₆H₄ |
| 38 | C₆H₅ | -C(O)-C₆H₄-4-Br | H | 4-OCF₃-C₆H₄ |
| 39 | C₆H₅ | -C(O)-C₆H₄-4-Br | H | 4-Cl-C₆H₄ |
| 40 | 4-F-C₆H₄ | -C(O)-C₆H₄-4-CH₃ | H | 4-Br-C₆H₄ |
| 41 | 4-F-C₆H₄ | -C(O)-C₆H₄-4-CH₃ | H | 4-F-C₆H₄ |
| 42 | 4-F-C₆H₄ | -C(O)-C₆H₄-4-CH₃ | H | 4-Cl-C₆H₄ |
| 43 | 4-F-C₆H₄ | -C(O)-C₆H₄-4-CH₃ | H | 4-CF₃-C₆H₄ |
| 44 | 4-F-C₆H₄ | -C(O)-C₆H₄-4-Cl | H | 4-Br-C₆H₄ |
| 45 | C₆H₅ | -C(O)-C₆H₄-2-Cl | H | 4-F-C₆H₄ |

-continued

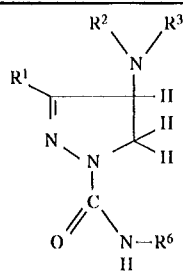
(XI)

| Ex. | R¹ | R² | R³ | R⁶ |
|---|---|---|---|---|
| 46 | phenyl | −C(O)−(2-Cl-phenyl) | H | 4-CF₃-phenyl |
| 47 | phenyl | −C(O)−(2-Cl-phenyl) | H | 4-Cl-phenyl |
| 48 | phenyl | −C(O)−(2-Cl-phenyl) | H | 4-Br-phenyl |
| 49 | phenyl | −C(O)−(4-Cl-phenyl) | H | 4-F-phenyl |
| 50 | 4-Cl-phenyl | −C(O)−phenyl | H | 4-Cl-phenyl |
| 51 | 4-F-phenyl | −C(O)−(4-Cl-phenyl) | H | 4-Br-phenyl |
| 52 | 4-Cl-phenyl | −C(O)−phenyl | H | 4-Br-phenyl |
| 53 | 4-Cl-phenyl | −C(O)−(4-F-phenyl) | H | 4-Br-phenyl |
| 54 | 4-Cl-phenyl | −C(O)−(4-Cl-phenyl) | H | 4-Cl-phenyl |
| 55 | 4-Br-phenyl | −C(O)−(4-Br-phenyl) | H | 4-F-phenyl |
| 56 | 4-Br-phenyl | −C(O)−(4-Br-phenyl) | H | 4-OCF₃-phenyl |

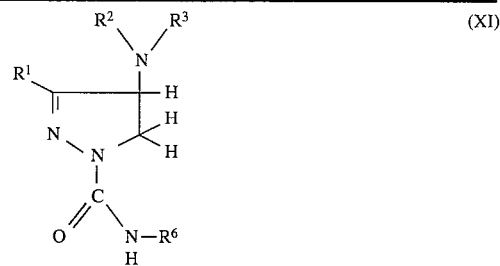
| Ex. | R¹ | R² | R³ | R⁶ |
|---|---|---|---|---|
| 57 | 4-Br-C₆H₄ | 4-Br-C₆H₄-C(O)- | H | 4-CF₃-C₆H₄ |
| 58 | 4-Br-C₆H₄ | 4-Br-C₆H₄-C(O)- | H | 4-OCHF₂-C₆H₄ |
| 59 | 4-Br-C₆H₄ | 4-Br-C₆H₄-C(O)- | H | 4-Cl-C₆H₄ |
| 60 | 4-Br-C₆H₄ | 4-Br-C₆H₄-C(O)- | H | 4-Br-C₆H₄ |
| 61 | 4-Cl-C₆H₄ | 4-CH₃-C₆H₄-C(O)- | H | 4-Br-C₆H₄ |
| 62 | 4-Cl-C₆H₄ | 4-CH₃-C₆H₄-C(O)- | H | 4-Cl-C₆H₄ |
| 63 | 4-Cl-C₆H₄ | C₆H₅-C(O)- | H | 4-CF₃-C₆H₄ |
| 64 | 4-Cl-C₆H₄ | C₆H₅-C(O)- | H | 4-OCF₃-C₆H₄ |
| 65 | 4-Cl-C₆H₄ | C₆H₅-C(O)- | H | 4-OCHF₂-C₆H₄ |
| 66 | 4-Br-C₆H₄ | 4-Cl-C₆H₄-C(O)- | H | 4-F-C₆H₄ |
| 67 | 4-Br-C₆H₄ | 4-Cl-C₆H₄-C(O)- | H | 4-OCF₃-C₆H₄ |
| 68 | 4-Br-C₆H₄ | 4-Cl-C₆H₄-C(O)- | H | 4-CF₃-C₆H₄ |

-continued
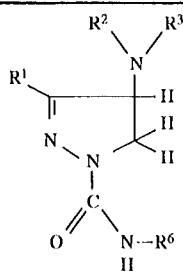
(XI)
| Ex. | R¹ | R² | R³ | R⁶ |
|---|---|---|---|---|
| 69 | —C₆H₄—Br | —C(=O)—C₆H₄—Cl | H | —C₆H₄—Cl |
| 70 | —C₆H₄—Br | —C(=O)—C₆H₄—Cl | H | —C₆H₄—Br |
| 71 | —C₆H₄—Br | —C(=O)—C₆H₄—Cl | H | —C₆H₄—OCHF₂ |
| 72 | —C₆H₄—Br | —C(=O)—C₆H₅ | H | —C₆H₄—F |
| 73 | —C₆H₄—Br | —C(=O)—C₆H₅ | H | —C₆H₄—OCF₃ |
| 74 | —C₆H₅ | —C(=O)—C₆H₄—Br | H | —C₆H₄—Br |
| 75 | —C₆H₄—Cl | —C(=O)—C₆H₄—CH₃ | H | —C₆H₄—F |
| 76 | —C₆H₄—Cl | —C(=O)—C₆H₄—CH₃ | H | —C₆H₄—OCF₃ |
| 77 | —C₆H₄—Cl | —C(=O)—C₆H₄—CH₃ | H | —C₆H₄—CF₃ |
| 78 | —C₆H₄—Cl | —C(=O)—C₆H₄—Cl | H | —C₆H₄—F |
| 79 | —C₆H₄—Cl | —C(=O)—C₆H₄—Cl | H | —C₆H₄—OCF₃ |
| 80 | —C₆H₄—Cl | —C(=O)—C₆H₄—Cl | H | —C₆H₄—CF₃ |

-continued
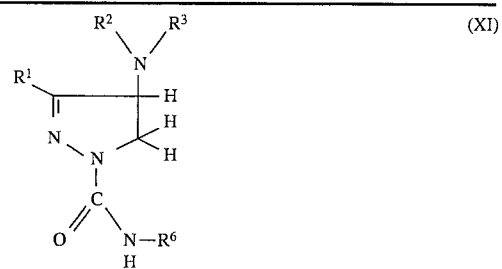
| Ex. | R¹ | R² | R³ | R⁶ |
|---|---|---|---|---|
| 81 | 4-Cl-C₆H₄ | -C(O)-C₆H₄-4-Cl | H | 4-OCHF₂-C₆H₄ |
| 82 | 4-Br-C₆H₄ | -C(O)-C₆H₅ | H | 4-CF₃-C₆H₄ |
| 83 | 4-Br-C₆H₄ | -C(O)-C₆H₅ | H | 4-Cl-C₆H₄ |
| 84 | 4-F-C₆H₄ | -C(O)-C₆H₄-4-CH₃ | H | 4-OCF₃-C₆H₄ |
| 85 | 4-F-C₆H₄ | -C(O)-C₆H₄-4-CH₃ | H | 4-OCHF₂-C₆H₄ |
| 86 | 4-Br-C₆H₄ | -C(O)-C₆H₅ | H | 4-Br-C₆H₄ |
| 87 | 4-Br-C₆H₄ | -C(O)-C₆H₅ | H | 4-OCF₃-C₆H₄ |
| 88 | 4-Cl-C₆H₄ | -C(O)-C₆H₄-4-F | H | 4-F-C₆H₄ |
| 89 | 4-Cl-C₆H₄ | -C(O)-C₆H₄-4-F | H | 4-OCF₃-C₆H₄ |
| 90 | 4-Cl-C₆H₄ | -C(O)-C₆H₄-4-F | H | 4-CF₃-C₆H₄ |
| 91 | C₆H₅ | -C(O)-C₆H₅ | H | 4-F-C₆H₄ |
| 92 | C₆H₅ | -C(O)-C₆H₅ | H | 4-Cl-C₆H₄ |

-continued
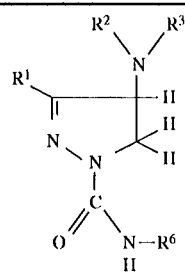
(XI)
| Ex. | R¹ | R² | R³ | R⁶ |
|---|---|---|---|---|
| 93 | –C₆H₅ | –C(=O)–C₆H₅ | H | –C₆H₄–Br |
| 94 | –C₆H₅ | –C(=O)–C₆H₄–F | H | –C₆H₄–Cl |
| 95 | –C₆H₅ | –C(=O)–C₆H₄–F | H | –C₆H₄–Br |
| 96 | –C₆H₅ | –C(=O)–C₆H₄(Cl) | H | –C₆H₄–OCF₃ |
| 97 | –C₆H₅ | –C(=O)–C₆H₄(Cl) | H | –C₆H₄–OCHF₂ |
| 98 | –C₆H₅ | –C(=O)–C₆H₄–F | H | –C₆H₄–F |
| 99 | –C₆H₅ | –C(=O)–C₆H₄(OCH₃) | H | –C₆H₄–F |
| 100 | –C₆H₅ | –C(=O)–C₆H₄(OCH₃) | H | –C₆H₄–OCF₃ |
| 101 | –C₆H₅ | –C(=O)–C₆H₄(OCH₃) | H | –C₆H₄–CF₃ |
| 102 | –C₆H₅ | –C(=O)–C₆H₄(OCH₃) | H | –C₆H₄–Cl |

-continued

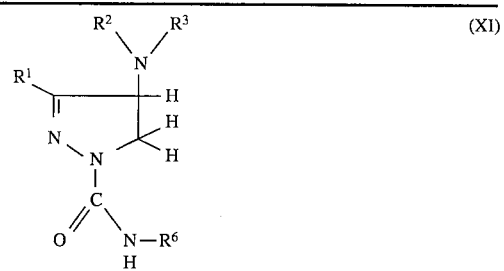

(XI)

| Ex. | R$^1$ | R$^2$ | R$^3$ | R$^6$ |
|---|---|---|---|---|
| 103 | phenyl | 2-CH$_3$O-C$_6$H$_4$-C(=O)- | H | 4-Br-C$_6$H$_4$- |
| 104 | phenyl | 2-CH$_3$O-C$_6$H$_4$-C(=O)- | H | 4-OCHF$_2$-C$_6$H$_4$- |
| 105 | 4-F-C$_6$H$_4$- | 4-Cl-C$_6$H$_4$-C(=O)- | H | 4-F-C$_6$H$_4$- |
| 106 | 4-F-C$_6$H$_4$- | 4-Cl-C$_6$H$_4$-C(=O)- | H | 4-OCF$_3$-C$_6$H$_4$- |
| 107 | 4-F-C$_6$H$_4$- | 4-Cl-C$_6$H$_4$-C(=O)- | H | 4-CF$_3$-C$_6$H$_4$- |
| 108 | 4-F-C$_6$H$_4$- | 4-Cl-C$_6$H$_4$-C(=O)- | H | 4-Cl-C$_6$H$_4$- |
| 109 | 4-F-C$_6$H$_4$- | 4-Cl-C$_6$H$_4$-C(=O)- | H | 4-OCHF$_2$-C$_6$H$_4$- |
| 110 | 4-Cl-C$_6$H$_4$- | 4-F-C$_6$H$_4$-C(=O)- | H | 4-Cl-C$_6$H$_4$- |
| 111 | 4-F-C$_6$H$_4$- | 4-F-C$_6$H$_4$-C(=O)- | H | 3-Cl-C$_6$H$_4$- |
| 112 | 4-F-C$_6$H$_4$- | 4-F-C$_6$H$_4$-C(=O)- | H | 3-CF$_3$-C$_6$H$_4$- |
| 113 | 4-F-C$_6$H$_4$- | 4-Br-C$_6$H$_4$-C(=O)- | H | 4-Br-C$_6$H$_4$- |

-continued
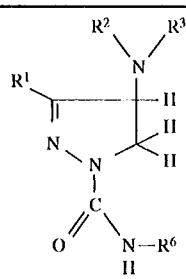
| Ex. | R¹ | R² | R³ | R⁶ |
|---|---|---|---|---|
| 114 | 4-F-C₆H₄ | -C(O)-C₆H₄-4-Br | H | 4-Cl-C₆H₄ |
| 115 | 4-Cl-C₆H₄ | -C(O)-C₆H₄-4-F | H | 3-CF₃-C₆H₄ |
| 116 | 4-Br-C₆H₄ | -C(O)-C₆H₄-4-F | H | 4-CF₃-C₆H₄ |
| 117 | 4-Br-C₆H₄ | -C(O)-C₆H₄-4-F | H | 4-F-C₆H₄ |
| 118 | 4-Br-C₆H₄ | -C(O)-C₆H₄-4-F | H | 3-CF₃-C₆H₄ |
| 119 | 4-Br-C₆H₄ | -C(O)-C₆H₄-4-F | H | 4-Br-C₆H₄ |
| 120 | 4-Br-C₆H₄ | -C(O)-C₆H₄-4-F | H | 4-Cl-C₆H₄ |
| 121 | 4-Cl-C₆H₄ | -C(O)-C₆H₄-2-Cl | H | 3-Cl-C₆H₄ |
| 122 | 4-Cl-C₆H₄ | -C(O)-C₆H₄-4-CH₃ | H | 3-CF₃-C₆H₄ |
| 123 | 4-Cl-C₆H₄ | -C(O)-C₆H₄-2-Cl | H | 3-CF₃-C₆H₄ |

-continued (XI)

Structure: pyrazoline ring with R¹ at C3, N(R²)(R³) at C4 (with H), CH₂ (H,H) at C5, N1-C(=O)-NH-R⁶

| Ex. | R¹ | R² | R³ | R⁶ |
|---|---|---|---|---|
| 124 | 4-F-C₆H₄- | -C(=O)-C₆H₄-4-Cl | H | 3-CF₃-C₆H₄- |
| 125 | 4-Cl-C₆H₄- | -C(=O)-C₆H₄-4-F | H | 3-Cl-C₆H₄- |
| 126 | 4-Br-C₆H₄- | -C(=O)-(CH₂)₅- | | 4-CF₃-C₆H₄- |
| 127 | 4-Br-C₆H₄- | -C(=O)-(CH₂)₅- | | 4-F-C₆H₄- |
| 128 | 4-Br-C₆H₄- | -C(=O)-(CH₂)₅- | | 4-OCF₃-C₆H₄- |
| 129 | 4-Br-C₆H₄- | -C(=O)-(CH₂)₅- | | 4-Cl-C₆H₄- |
| 130 | 4-Br-C₆H₄- | -C(=O)-(CH₂)₅- | | 4-Br-C₆H₄- |
| 131 | 4-Br-C₆H₄- | -C(=O)-(CH₂)₅- | | 4-OCHF₂-C₆H₄- |
| 132 | 4-Br-C₆H₄- | -C(=O)-(CH₂)₅- | | 4-CF₃-C₆H₄- |
| 133 | 4-Cl-C₆H₄- | -C(=O)-CH₃ | H | 4-CF₃-C₆H₄- |
| 134 | 4-Cl-C₆H₄- | -C(=O)-CH₂-CH(CH₃)₂ | H | 4-OCF₃-C₆H₄- |

In entries 126–132, R² and R³ together form -C(=O)-(CH₂)₅- (cyclic).

-continued (XI)

| Ex. | R¹ | R² | R³ | R⁶ |
|---|---|---|---|---|
| 135 | 4-Cl-C₆H₄- | -C(O)-CH₂-CH(CH₃)₂ | H | 4-CF₃-C₆H₄- |
| 136 | 4-Cl-C₆H₄- | -C(O)-CH₂-CH(CH₃)₂ | H | 4-Cl-C₆H₄- |
| 137 | 4-Cl-C₆H₄- | -C(O)-CH₂-CH(CH₃)₂ | H | 4-F-C₆H₄- |
| 138 | 4-Cl-C₆H₄- | -C(O)-CH₂-CH(CH₃)₂ | H | 4-Br-C₆H₄- |
| 139 | 4-Cl-C₆H₄- | -C(O)-CH₂-CH(CH₃)₂ | H | 4-(OCHF₂)-C₆H₄- |
| 140 | 4-Cl-C₆H₄- | -C(O)-CH₃ | H | 4-F-C₆H₄- |
| 141 | 4-Cl-C₆H₄- | -C(O)-CH₂-CH₃ | H | 4-(OCF₃)-C₆H₄- |
| 142 | 4-Cl-C₆H₄- | -C(O)-CH₂-CH₃ | H | 4-Cl-C₆H₄- |
| 143 | 4-Cl-C₆H₄- | -C(O)-CH₂-CH₃ | H | 4-Br-C₆H₄- |
| 144 | 4-F-C₆H₄- | -C(O)-OCH₃ | H | 4-Br-C₆H₄- |
| 145 | 4-F-C₆H₄- | -C(O)-CH₂-CH(CH₃)₂ | H | 4-F-C₆H₄- |
| 146 | 4-Br-C₆H₄- | -C(O)-(CH₂) | H | 4-CF₃-C₆H₄- |

-continued
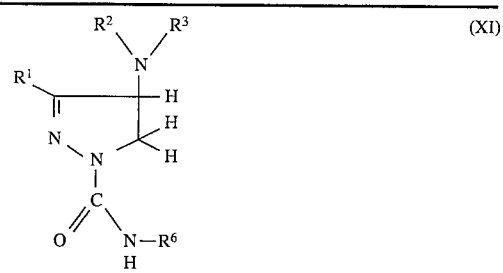
(XI)
| Ex. | R¹ | R² | R³ | R⁶ |
|---|---|---|---|---|
| 147 | 4-Cl-C₆H₄ | -C(=O)-CH₂-CH(CH₃)₂ | H | 4-CF₃-C₆H₄ |
| 148 | 4-Cl-C₆H₄ | -C(=O)-CH(CH₃)₂ | H | 4-CF₃-C₆H₄ |
| 149 | 4-F-C₆H₄ | -C(=O)-CH₂-CH(CH₃)₂ | H | 4-OCF₃-C₆H₄ |
| 150 | 4-F-C₆H₄ | -C(=O)-CH₂-CH(CH₃)₂ | H | 4-Br-C₆H₄ |
| 151 | 4-F-C₆H₄ | -C(=O)-CH₂-CH(CH₃)₂ | H | 4-O-CHF₂-C₆H₄ |
| 152 | 4-F-C₆H₄ | -C(=O)-CH₂-CH(CH₃)₂ | H | 4-O-CF₃-C₆H₄ |
| 153 | 4-Cl-C₆H₄ | -C(=O)-CH(CH₃)₂ | H | 4-O-CF₃-C₆H₄ |
| 154 | 4-Cl-C₆H₄ | -C(=O)-CH(CH₃)₂ | H | 4-CF₃-C₆H₄ |
| 155 | 4-Cl-C₆H₄ | -C(=O)-CH(CH₃)₂ | H | 4-F-C₆H₄ |
| 156 | 4-Cl-C₆H₄ | -C(=O)-CH(CH₃)₂ | H | 4-Cl-C₆H₄ |
| 157 | 4-Cl-C₆H₄ | -C(=O)-CH(CH₃)₂ | H | 4-Br-C₆H₄ |

-continued
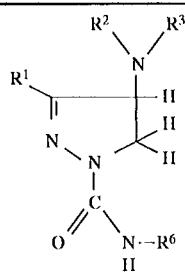 (XI)
| Ex. | R¹ | R² | R³ | R⁶ |
|---|---|---|---|---|
| 158 | 4-Cl-C₆H₄– | –C(O)–CH(CH₃)₂ | H | 4-(OCHF₂)-C₆H₄– |
| 159 | 4-Cl-C₆H₄– | –C(O)–CH(CH₃)₂ | H | 4-(SCF₃)-C₆H₄– |
| 160 | 4-Cl-C₆H₄– | –C(O)–CH(CH₃)₂ | H | 3-Cl-4-F-C₆H₃– |
| 161 | 4-Cl-C₆H₄– | –C(O)–CH(CH₃)₂ | H | 3-Cl-C₆H₄– |
| 162 | 4-Br-C₆H₄– | –C(O)–(CH₂)₃– | | 4-F-C₆H₄– |
| 163 | 4-Br-C₆H₄– | –C(O)–(CH₂)₃– | | 4-(OCF₃)-C₆H₄– |
| 164 | 4-Br-C₆H₄– | –C(O)–(CH₂)₃– | | 4-Cl-C₆H₄– |
| 165 | 4-Br-C₆H₄– | –C(O)–CH₃ | H | 4-CF₃-C₆H₄– |
| 166 | 4-Br-C₆H₄– | –C(O)–CH₃ | H | 4-Cl-C₆H₄– |
| 167 | 4-Br-C₆H₄– | –C(O)–OCH₃ | H | 4-(OCF₃)-C₆H₄– |
| 168 | 4-Cl-C₆H₄– | –C(O)–cyclopropyl | H | 4-Br-C₆H₄– |

-continued $$\text{(XI)}$$

Structure XI: pyrazoline ring with R¹ at C3 position, NR²R³ at C4 (with H), CH₂ at C5, N1 bearing C(=O)NH-R⁶.

| Ex. | R¹ | R² | R³ | R⁶ |
|---|---|---|---|---|
| 169 | 4-Br-C₆H₄ | —C(=O)—(CH₂)₃— | | 4-Br-C₆H₄ |
| 170 | 4-Br-C₆H₄ | —C(=O)—(CH₂)₃— | | 4-(OCHF₂)-C₆H₄ |
| 171 | 4-Cl-C₆H₄ | —C(=O)—CH₂—CH(CH₃)₂ | H | 4-Cl-C₆H₄ |
| 172 | 4-Cl-C₆H₄ | —C(=O)—C₂H₅ | H | 4-(OCHF₂)-C₆H₄ |
| 173 | 4-Br-C₆H₄ | —C(=O)-cyclopropyl | H | 4-F-C₆H₄ |
| 174 | 4-Br-C₆H₄ | —C(=O)-cyclopropyl | H | 4-(OCF₃)-C₆H₄ |
| 175 | 4-F-C₆H₄ | —C(=O)—CH(CH₃)₂ | H | 4-F-C₆H₄ |
| 176 | 4-F-C₆H₄ | —C(=O)—CH(CH₃)₂ | H | 4-(OCF₃)-C₆H₄ |
| 177 | 4-Br-C₆H₄ | —C(=O)-cyclopropyl | H | 4-CF₃-C₆H₄ |
| 178 | 4-Br-C₆H₄ | —C(=O)-cyclopropyl | H | 4-Cl-C₆H₄ |
| 179 | 4-Br-C₆H₄ | —C(=O)-cyclopropyl | H | 4-Br-C₆H₄ |
| 180 | 4-F-C₆H₄ | —C(=O)—CH(CH₃)₂ | H | 4-CF₃-C₆H₄ |

|     |     |     | (XI) |
| --- | --- | --- | --- |

| Ex. | R¹ | R² | R³ | R⁶ |
| --- | --- | --- | --- | --- |
| 181 | 4-F-C₆H₄- | -C(=O)-CH(CH₃)₂ | H | 4-Cl-C₆H₄- |
| 182 | 4-F-C₆H₄- | -C(=O)-CH(CH₃)₂ | H | 4-(OCHF₂)-C₆H₄- |

PREPARATION EXAMPLES FOR COMPOUNDS OF FORMULA (I)

EXAMPLE 190

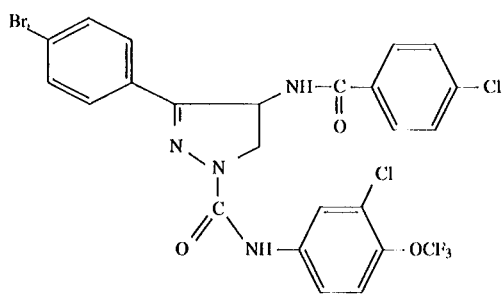

(Process (a))

1.52 g (0.00642 mol) of 3-chloro-4-trifluoromethoxyphenyl isocyanate are added dropwise at room temperature with stirring to 2.26 g (0.00598 mol) of 3-(4-bromophenyl)-4-[(4-chlorophenyl)-carbonylamino]-4,5-dihydropyrazole in 50 ml of dichloromethane, and the mixture is refluxed for one hour. For working-up, the reaction mixture is cooled and precipitated solid is filtered off with suction and dried.

2.18 g (51% of theory) of 3-(4-bromophenyl)-4-[ (4-chlorophenyl)-carbonylamino]-1-[(3-chloro-4-trifluoromethoxyphenyl)-aminocarbonyl]-4,5-dihydropyrazole of melting point >200° C. are obtained.

¹H NMR (DMSO-d₆/tetramethylsilane): δ=3.93; 4.26; 5.97; 9.54; 9.38 ppm

The following substituted pyrazolines of the general formula (I)

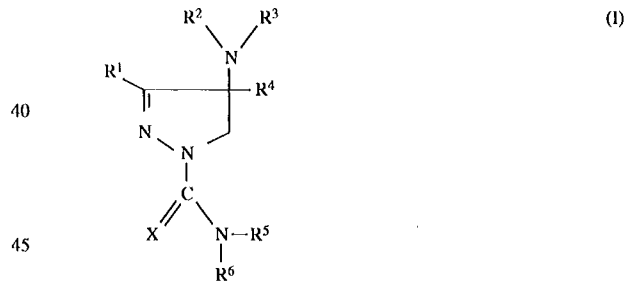

are obtained in an analogous manner and following the general preparation instructions:

| Ex. No. | R¹ | R² | R³ | R⁴ | R⁵ | R⁶ | X | ¹H NMR*⁾ |
| --- | --- | --- | --- | --- | --- | --- | --- | --- |
| 192 | 4-Cl-C₆H₄- | -C(=O)-C₆H₄-Cl | H | H | H | 2-F-C₆H₄- | O | 3.92; 4.25; 5.98; 9.37 9.39 |
| 193 | 4-Cl-C₆H₄- | -C(=O)-C₆H₄-Cl | H | H | H | 2-CF₃-C₆H₄-CF₃ | O | 3.96; 4.29 6.00; 9.39 9.90 |

-continued

| Ex. No. | R¹ | R² | R³ | R⁴ | R⁵ | R⁶ | X | ¹H NMR*⁾ |
|---|---|---|---|---|---|---|---|---|
| 194 | 4-F-phenyl | 2-Cl-benzoyl | H | H | H | 3-CF₃-4-CF₃-phenyl | O | 3.96; 4.30; 5.96; 9.31; 9.84 |
| 195 | 4-Cl-phenyl | 4-Cl-benzoyl | H | H | H | 3-CF₃-4-Cl-phenyl | O | 3.94; 4.26; 5.99; 9.38; 9.44 |
| 196 | 4-F-phenyl | 2-Cl-benzoyl | H | H | H | 3-Cl-4-CF₃-phenyl | O | 3.95; 4.29; 5.95; 9.31; 9.65 |
| 197 | 4-Cl-phenyl | 4-Cl-benzoyl | H | H | H | 3-CN-2-F-phenyl | O | 3.94; 4.26; 5.98; 9.49; 9.63 |
| 198 | 4-F-phenyl | 2-Cl-benzoyl | H | H | H | 3-CF₃-4-Cl-phenyl | O | 3.94; 4.27; 5.95; 9.31; 9.58 |
| 199 | 4-F-phenyl | 2-Cl-benzoyl | H | H | H | 3-Cl-4-OCF₃-phenyl | O | 3.93; 4.27; 5.95; 9.31; 9.48 |
| 200 | 4-F-phenyl | 2-Cl-benzoyl | H | H | H | 3-Cl-4-CH₃-phenyl | O | 3.91; 4.25; 5.93; 9.21; 9.30 |
| 201 | 4-F-phenyl | 2-Cl-benzoyl | H | H | H | 3-Cl-4-OCF₃-phenyl | O | 3.93; 4.26; 5.94; 9.31; 9.33 |
| 202 | 4-F-phenyl | 2-Cl-benzoyl | H | H | H | 3-Cl-4-CF₃-phenyl | O | 3.95; 4.28; 5.94; 9.41; 9.73 |
| 203 | 4-F-phenyl | 2-Cl-benzoyl | H | H | H | 3-F-4-F-phenyl | O | 3.92; 4.25; 5.95; 9.30; 9.34 |
| 204 | 4-F-phenyl | 4-F-benzoyl | H | H | H | 3-CF₃-4-Cl-phenyl | O | 3.93; 4.26; 6.00; 9.32; 9.61 |

-continued

| Ex. No. | R¹ | R² | R³ | R⁴ | R⁵ | R⁶ | X | ¹H NMR*) |
|---|---|---|---|---|---|---|---|---|
| 205 | 4-F-C₆H₄ | -C(O)-C₆H₄-4-F | H | H | H | 2-F-6-CN-C₆H₃ | O | 3.93; 4.26; 6.00; 9.33; 9.52 |
| 206 | 4-F-C₆H₄ | -C(O)-C₆H₄-4-F | H | H | H | 2,3-di-F-C₆H₃ | O | 3.92; 4.25; 5.98; 9.36; 9.37 |
| 207 | 4-F-C₆H₄ | -C(O)-C₆H₄-4-F | H | H | H | 3-Cl-4-OCHF₂-C₆H₃ | O | 3.92; 4.25; 5.99; 9.36; 9.40 |
| 208 | 4-F-C₆H₄ | -C(O)-C₆H₄-4-F | H | H | H | 3,4-di-Cl-C₆H₃ | O | 3.91; 4.25; 5.99; 9.32; 9.44 |
| 209 | 4-Cl-C₆H₄ | -C(O)-C₆H₄-4-F | H | H | H | 4-CF₃-C₆H₄ | O | 3.77; 4.14; 5.94; 9.23 |
| 210 | 4-Cl-C₆H₄ | -C(O)-C₆H₄-4-F | H | H | H | 3-Cl-4-OCF₃-C₆H₃ | O | 3.93; 4.27; 6.00; 9.53; 9.30 |
| 211 | 4-Cl-C₆H₄ | -C(O)-C₆H₄-3-OCH₃ | H | H | H | 4-CF₃-C₆H₄ | O | 3.78; 4.15; 5.93; 9.20 |
| 212 | 4-Cl-C₆H₄ | -C(O)-C₆H₄-3-OCH₃ | H | H | H | 3-Cl-4-OCF₃-C₆H₃ | O | 3.94; 4.27; 6.01; 9.53; 9.26 |
| 213 | 4-Cl-C₆H₄ | -C(O)-C₆H₄-4-CH₃ | H | H | H | 4-CF₃-C₆H₄ | O | 3.78; 4.14; 5.93; 6.67; 6.96; 9.14 |
| 214 | 4-Cl-C₆H₄ | -C(O)-C₆H₄-2-Cl | H | H | H | 4-CF₃-C₆H₄ | O | 3.83; 4.15; 5.86; 6.67; 6.95; 9.27 |
| 215 | 4-Cl-C₆H₄ | -C(O)-C₆H₄-2-Cl | H | H | H | 3-Cl-4-OCF₃-C₆H₃ | O | 3.93; 4.28; 5.95; 9.52; 9.33 |

| Ex. No. | R¹ | R² | R³ | R⁴ | R⁵ | R⁶ | X | ¹H NMR*) |
|---|---|---|---|---|---|---|---|---|
| 216 | 4-F-C₆H₄- | -C(O)-C₆H₅ | H | H | H | 3-Cl-4-OCF₃-C₆H₃- | O | 3.92; 4.30; 6.00; 9.50; 9.29 |
| 217 | 4-F-C₆H₄- | -C(O)-C₆H₄-4-F | H | H | H | 4-CF₃-C₆H₁₀- | O | 3.76; 4.13; 5.95; 6.93; 9.24 |
| 218 | 4-F-C₆H₄- | -C(O)-C₆H₄-4-F | H | H | H | 3-Cl-4-OCF₃-C₆H₃- | O | 3.93; 4.26; 6.00; 9.51; 9.36 |
| 219 | 4-Cl-C₆H₄- | -C(O)-C₆H₅ | H | H | H | 4-CF₃-C₆H₁₀- | O | 4.15; 6.68; 9.23 |
| 220 | 4-Cl-C₆H₄- | -C(O)-C₆H₅ | H | H | H | 3-Cl-4-OCF₃-C₆H₃- | O | 3.93; 4.27; 6.00; 9.32; 9.28 |
| 221 | 4-Br-C₆H₄- | -C(O)-C₆H₄-4-Br | H | H | H | 3-Cl-4-OCF₃-C₆H₃- | O | 3.92; 4.25; 5.97; 9.53; 9.35 |
| 222 | 4-Br-C₆H₄- | -C(O)-C₆H₄-4-Br | H | H | H | 4-CF₃-C₆H₁₀- | O | 4.13; 6.96; 9.32; 9.10 |
| 223 | 4-Br-C₆H₄- | -C(O)-C₆H₄-4-Cl | H | H | H | 3-Cl-4-OCF₃-C₆H₃- | O | 3.93; 4.26; 5.97; 9.54; 9.38 |
| 224 | 4-Cl-C₆H₄- | -C(O)-C₆H₄-4-CH₃ | H | H | H | 3-Cl-4-OCF₃-C₆H₃- | O | 3.90; 4.26; 5.98; 9.18; 9.51 |
| 225 | 4-Cl-C₆H₄- | -C(O)-C₆H₄-4-Cl | H | H | H | 3-Cl-4-OCF₃-C₆H₃- | O | 3.94; 4.26; 5.98; 9.40; 9.53 |
| 226 | 4-Br-C₆H₄- | -C(O)-C₆H₅ | H | H | H | 4-CF₃-C₆H₁₀- | O | 3.80; 4.15; 5.92; 6.68; 9.24 |
| 227 | C₆H₅- | -C(O)-C₆H₄-4-CH₃ | H | H | H | 3-Cl-4-OCF₃-C₆H₃- | O | 3.90; 4.28; 6.01; 9.52; 9.20 |

-continued

| Ex. No. | R¹ | R² | R³ | R⁴ | R⁵ | R⁶ | X | ¹H NMR*) |
|---|---|---|---|---|---|---|---|---|
| 228 | 4-F-C₆H₄- | 4-CH₃-C₆H₄-C(O)- | H | H | H | 4-CF₃-cyclohexyl | O | 4.13; 5.93; 6.64; 6.92; 9.15 |
| 229 | C₆H₅- | 2-Cl-C₆H₄-C(O)- | H | H | H | 4-CF₃-cyclohexyl | O | 4.14; 5.88; 6.62; 6.88; 9.26 |
| 230 | C₆H₅- | 2-Cl-C₆H₄-C(O)- | H | H | H | 3-Cl-4-OCF₃-C₆H₃- | O | 3.93; 4.28; 5.97; 9.32; 9.48 |
| 231 | C₆H₅- | 2-CH₃O-C₆H₄-C(O)- | H | H | H | 4-CF₃-cyclohexyl | O | 4.14; 5.97; 6.90; 9.20 |
| 232 | 4-F-C₆H₄- | 4-Cl-C₆H₄-C(O)- | H | H | H | 4-CF₃-cyclohexyl | O | 3.82; 4.15; 5.95 6.67; 9.32 |
| 233 | 4-F-C₆H₄- | 4-Cl-C₆H₄-C(O)- | H | H | H | 3-Cl-4-OCF₃-C₆H₃- | O | 3.95; 4.27; 6.00; 9.52; 9.39 |
| 234 | 4-F-C₆H₄- | 4-F-C₆H₄-C(O)- | H | H | H | 3-Cl-4-CH₃-C₆H₃- | O | 3.91; 4.24; 5.99; 9.24; 9.32 |
| 235 | 4-F-C₆H₄- | 4-Br-C₆H₄-C(O)- | H | H | H | 3-Cl-4-CH₃-C₆H₃- | O | 3.91; 4.24; 6.00; 9.24; 9.34 |
| 236 | 4-F-C₆H₄- | 4-F-C₆H₄-C(O)- | H | H | H | 3-Cl-4-F-C₆H₃- | O | 3.92; 4.25; 5.99; 9.34; 9.37 |
| 237 | 4-Cl-C₆H₄- | 4-F-C₆H₄-C(O)- | H | H | H | 3-CN-4-F-C₆H₃- | O | 3.93; 4.27; 6.00; 9.30; 9.54 |
| 238 | 4-Cl-C₆H₄- | 4-F-C₆H₄-C(O)- | H | H | H | 2,3-(CF₃)₂-C₆H₃- | O | 3.97; 4.30; 6.02; 9.31; 9.89 |

-continued

| Ex. No. | R¹ | R² | R³ | R⁴ | R⁵ | R⁶ | X | ¹H NMR*) |
|---|---|---|---|---|---|---|---|---|
| 239 | 4-Br-phenyl | —C(=O)—(4-F-phenyl) | H | H | H | 3-Cl-4-CH₃-phenyl | O | 3.91; 4.24; 5.98; 9.28; 9.32 |
| 240 | 4-Cl-phenyl | —C(=O)—(4-F-phenyl) | H | H | H | 3,4-Cl₂-phenyl | O | 3.93; 4.26; 5.99; 9.29; 9.47 |
| 241 | 4-F-phenyl | —C(=O)—(2-Cl-phenyl) | H | H | H | 3,4-Cl₂-phenyl | O | 3.93; 4.26; 5.95; 9.31; 9.42 |
| 242 | 4-Br-phenyl | —C(=O)—(CH₂)₅— | | H | H | 3,4-(OCF₂O)-phenyl | O | 3.61; 4.02 3.86; 4.14; 6.43; 9.54 |
| 243 | 4-F-phenyl | —C(=O)—CH₂—CH(CH₃)₂ | H | H | H | 4-CF₃-cyclohexyl | O | 5.69; — 8.60 |
| 244 | 4-F-phenyl | —C(=O)—CH₂—CH(CH₃)₂ | H | H | H | 3,4-(CF₃)₂-phenyl | O | 3.77; 4.15 5.78; 8.68 9.83 |
| 245 | 4-F-phenyl | —C(=O)—CH₂—CH(CH₃)₂ | H | H | H | 3,4-F₂-phenyl | O | 3.74; 4.14 5.74; 8.67 9.32 |
| 246 | 4-F-phenyl | —C(=O)—CH₂—CH(CH₃)₂ | H | H | H | 3-CF₃-4-Cl-phenyl | O | 3.74; 4.16 5.76; 8.68 9.57 9.49 |
| 247 | 4-Cl-phenyl | —C(=O)—CH(CH₃)₂ | H | H | H | 4-CF₃-cyclohexyl | O | 3.61; 4.03 5.68; 7.78 8.55 |
| 248 | 4-Cl-phenyl | —C(=O)—CH(CH₃)₂ | H | H | H | 3-Cl-4-OCF₃-phenyl | O | 3.74; 4.17 5.76; 8.63 3.74; 4.17 |
| 249 | 4-Cl-phenyl | —C(=O)—CH(CH₃)₂ | H | H | H | 3-Cl-4-CF₃-phenyl | O | 5.76; 8.61 9.59 |

-continued

| Ex. No. | R¹ | R² | R³ | R⁴ | R⁵ | R⁶ | X | ¹H NMR*) |
|---|---|---|---|---|---|---|---|---|
| 250 | 4-Cl-C₆H₄- | -C(=O)-CH(CH₃)₂ | H | H | H | 3-F, 2-CN-C₆H₃- | O | 3.74; 4.17 5.75; 8.61 9.50 |
| 251 | 4-Cl-C₆H₄- | -C(=O)-CH(CH₃)₂ | H | H | H | 4-OCHF₂, 2-Cl-C₆H₃- | | 3.73; 4.16 5.75; 8.60 9.38 |
| 252 | 4-Cl-C₆H₄- | -C(=O)-CH(CH₃)₂ | H | H | H | 3-F, 4-Cl-C₆H₃- | O | 3.72; 4.15 5.74; 8.60 9.35 |
| 253 | 4-Cl-C₆H₄- | -C(=O)-CH(CH₃)₂ | H | H | H | 3-CH₃, 4-Cl-C₆H₃- | O | 9.36 3.74; 4.15 5.75; 8.60 9.23 |
| 254 | 4-Cl-C₆H₄- | -C(=O)-CH(CH₃)₂ | H | H | H | 3,4-(O-CF₂-O)-C₆H₃- | O | 3.73; 4.16 5.74; 8.61 |
| 255 | 4-Br-C₆H₄- | -C(=O)-CH₃ | H | H | H | 3,4-(O-CF₂-O)-C₆H₃- | O | 3.75; 4.13 5.71; 8.70 9.36 |
| 256 | 4-Cl-C₆H₄- | -C(=O)-CH(CH₃)₂ | H | H | H | 3,4-(O-CF₂-O-CF₂)-C₆H₃- | O | 3.75; 4.18 5.75; 8.62 9.47 |
| 257 | 4-Br-C₆H₄- | -C(=O)-(CH₂)₃- | H | H | H | 3-OCF₃, 4-Cl-C₆H₃- | O | 4.05; 4.11 6.03; 8.06 |

*)The ¹H NMR spectra were recorded in hexadeuterodimethyl sulphoxide (DMSO-d₆) with tetramethylsilane (TMS) as the internal standard. The data given is the chemical shift as δ value in ppm.

| Ex. No. | R¹ | R² | R³ | R⁴ | R⁵ | R⁶ | X | Physical properties |
|---|---|---|---|---|---|---|---|---|
| 258 | 4-Br-C₆H₄- | -C(=O)-(CH₂)₃- | H | H | | 3-CF₃, 4-Cl-C₆H₃- | O | m.p.: 182° C. |

-continued

| Ex. No. | R$^1$ | R$^2$ | R$^3$ | R$^4$ | R$^5$ | R$^6$ | X | Physical properties |
|---|---|---|---|---|---|---|---|---|
| 259 | 4-Br-C$_6$H$_4$ | -C(O)-(CH$_2$)$_3$- | | H | H | 3,4-Cl$_2$-C$_6$H$_3$ | O | m.p.: 220° C. |
| 260 | 4-F-C$_6$H$_4$ | -C(O)-OCH$_3$ | H | H | H | 3-Cl-4-OCF$_3$-C$_6$H$_3$ | O | m.p.: 200° C. |
| 261 | 4-Cl-C$_6$H$_4$ | -C(O)-(CH$_2$)$_3$- | | H | H | 3-Cl-4-OCHF$_2$-C$_6$H$_3$ | O | m.p.: 194° C. |
| 262 | 4-Br-C$_6$H$_4$ | -C(O)-OCH$_3$ | H | H | H | 3-Cl-4-CF$_3$-C$_6$H$_3$ | O | m.p.: >200° C. |
| 263 | 4-F-C$_6$H$_4$ | -C(O)-CH$_3$ | H | H | H | 3-Cl-4-F-C$_6$H$_3$ | O | m.p.: >200° C. |
| 264 | 4-Cl-C$_6$H$_4$ | -C(O)-OCH$_3$ | H | H | H | 3-Cl-4-OCF$_3$-C$_6$H$_3$ | O | m.p.: >200° C. |
| 265 | 4-Cl-C$_6$H$_4$ | -C(O)-O-C(CH$_3$)$_2$-CCl$_3$ | H | H | H | 3-Cl-4-OCF$_3$-C$_6$H$_3$ | O | m.p.: 118° C. |
| 266 | 4-Br-C$_6$H$_4$ | -C(O)-(CH$_2$)$_3$- | | H | H | 3-Cl-4-F-C$_6$H$_3$ | O | m.p.: 170° C. |
| 267 | 4-F-C$_6$H$_4$ | -C(O)-CH$_3$ | H | H | H | 3-Cl-4-OCHF$_2$-C$_6$H$_3$ | O | m.p.: >200° C. |
| 268 | 4-F-C$_6$H$_4$ | -C(O)-C$_2$H$_5$ | H | H | H | 3-Cl-4-CF$_3$-C$_6$H$_3$ | O | m.p.: >200° C. |
| 269 | 4-Br-C$_6$H$_4$ | -C(O)-C$_2$H$_5$ | H | H | H | 3-Cl-4-OCF$_3$-C$_6$H$_3$ | O | m.p.: >200° C. |

-continued

| Ex. No. | R¹ | R² | R³ | R⁴ | R⁵ | R⁶ | X | Physical properties |
|---|---|---|---|---|---|---|---|---|
| 270 | 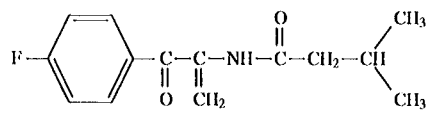 | —C(=O)—C₂H₅ | H | H | H | 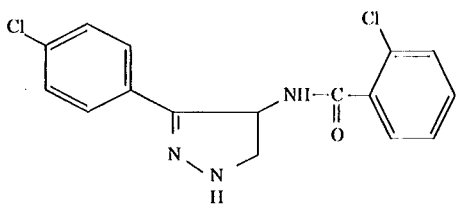 | O | m.p.: >200° C. |

(Note: R¹ = 4-fluorophenyl; R⁶ = 2-chlorophenyl; R² = —C(=O)—C₂H₅)

PREPARATION OF THE STARTING COMPOUNDS

EXAMPLE II-1

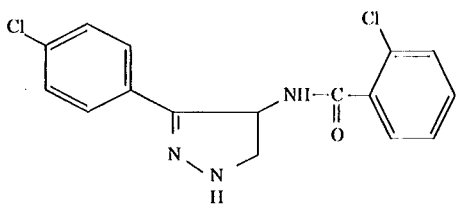

8.0 g (0.0856 mol) of N,N-dimethylmethyleneimmonium chloride are added at room temperature with stirring to 20 g (0.065 mol) of 2-chloro-N-[2-(4-chlorophenyl)-2-oxoethyl]-benzamide (preparation cf., for example, J. Amer. Chem. Soc. 77, 1850 [1955]) in 100 ml of acetonitrile, and the mixture is refluxed for 3 to 5 hours. When the starting compound can no longer be detected in the thin-layer chromatogram of the reaction mixture, 6.5 ml of hydrazine hydrate are added, and the mixture is refluxed for a further 4 to 6 hours. For working-up, the reaction mixture is cooled and precipitated solid is filtered off with suction, washed first with diethyl ether and then with water, and dried.

10.4 g (48% of theory) of 3-(4-chlorophenyl)-4-[(2-chlorophenyl)-carbonylamino]-4,5-dihydropyrazole are obtained as a brown solid which can be used in the subsequent reaction without further purification.

¹H-NMR (DMSO-d₆/tetramethylsilane): δ 5.68; 9.10 ppm

EXAMPLE II-2

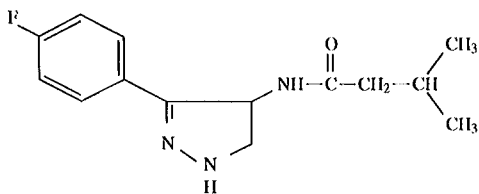

29 ml of hydrazine hydrate are added at 40°–50° C. with stirring to 37.0 g (0.149 mol) of 4'-fluoro-2-isobutylcarbonylaminoacrylophenone in 150 ml of ethanol, and the mixture is stirred for a further hour at 50° C. For working-up, the reaction mixture is concentrated in vacuo, and the product which precipitates during this process is filtered off with suction and dried.

37.0 g (95% of theory) and 3-(4-fluorophenyl)-4-isobutylcarbonylamino-4,5-dihydropyrazole are obtained as a yellow solid which can be reacted further directly without additional purification.

EXAMPLE VIII-1

F—C₆H₄—C(=O)—C(=CH₂)—NH—C(=O)—CH₂—CH(CH₃)₂

50 ml of 37% strength aqueous formaldehyde solution, 1 ml of piperidine and 1 ml of glacial acetic acid are added in succession with stirring at 60° C. to 37.4 g (0.158 mol) of 2-isobutylcarbonylamino-4'-fluoroacetophenone (preparation cf., for example, DE 2,947,140; J. Heterocycl. Chem. 24, 297–301 [1987]) in 240 ml of methanol, the mixture is subsequently stirred for a further hour at 60° C., and the solvent is then removed in vacuo.

37.0 g (94% of theory) of 4'-fluoro-2-isobutylcarbonylaminoacrylophenone are obtained as a solid which can be reacted further directly without additional purification.

The following pyrazolines of the general formula (XXX) which are unsubstituted in the 1-position are obtained in an analogous manner:

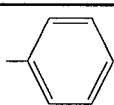
| Ex. No. | R¹ | R² | R³ | R⁴ | ¹H-NMR*⁾ |
|---|---|---|---|---|---|
| II-3 | 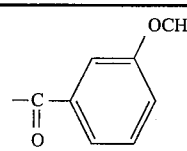 | 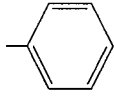 | H | H | 5.80; 9.02 |
| II-4 | 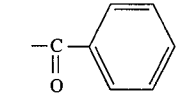 | 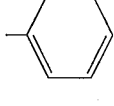 | H | H | 5.82; 9.09 |
| II-5 | 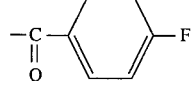 | 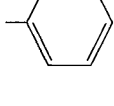 | H | H | 5.77; 9.06 |
| II-6 | 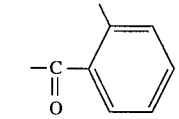 | 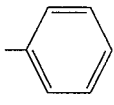 | H | H | 5.70; 9.09 |
| II-7 | 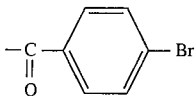 | 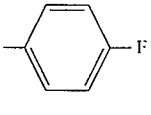 | H | H | 5.75; 9.13 |
| II-8 | 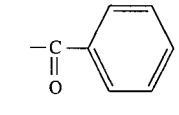 | 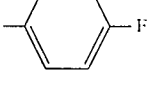 | H | H | 5.69; 9.08 |
| II-9 | 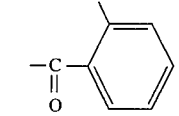 | 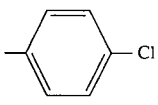 | H | H | 5.84; 9.08 |
| II-10 | 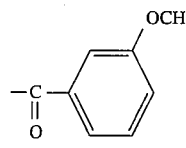 | 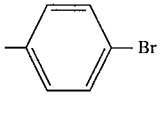 | H | H | 5.77; 9.01 |
| II-11 | 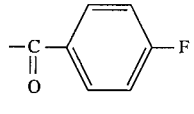 | 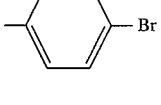 | H | H | 5.74; 9.03 |
| II-12 | 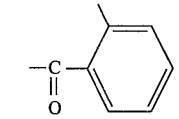 | 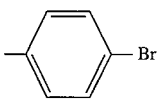 | H | H | 5.67; 9.07 |
| II-13 | 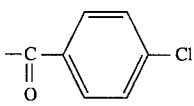 | | H | H | 5.74; 9.09 |

-continued
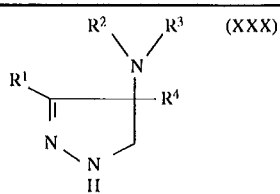
(XXX)
| Ex. No. | R¹ | R² | R³ | R⁴ | ¹H-NMR*⁾ |
|---|---|---|---|---|---|
| II-14 | 4-Br-C₆H₄– | –C(=O)–C₆H₄–Br | H | H | 5.74; 9.11 |
| II-15 | 4-Br-C₆H₄– | –C(=O)–C₆H₅ | H | H | 5.77; 9.01 |
| II-16 | 4-F-C₆H₄– | –C(=O)–C₆H₄–F | H | H | 5.76; 9.06 |
| II-17 | 4-F-C₆H₄– | –C(=O)–C₆H₄–Cl | H | H | 5.75; 9.11 |
| II-18 | 4-F-C₆H₄– | –C(=O)–C₆H₄–Br | H | H | 5.74; 9.12 |
| II-19 | 4-Cl-C₆H₄– | –C(=O)–C₆H₄–Br | H | H | 5.77; 8.96 |
| II-20 | 4-F-C₆H₄– | –C(=O)–C₆H₄–CH₃ | H | H | 5.78; 8.93 |
| II-21 | 4-Cl-C₆H₄– | –C(=O)–C₆H₄–Cl | H | H | 5.76; 9.11 |
| II-22 | 4-Cl-C₆H₄– | –C(=O)–C₆H₄–F | H | H | 5.75; 9.04 |
| II-23 | 4-Cl-C₆H₄– | –C(=O)–C₆H₄–CH₃ | H | H | 5.75; 8.92 |
| II-24 | 4-Br-C₆H₄– | –C(=O)–(CH₂)₅– | | H | 6.12; 7.68 |
| II-25 | 4-Cl-C₆H₄– | –C(=O)–CH₂–CH(CH₃)₂ | H | H | 5.49; 8.40 |
| II-26 | 4-Cl-C₆H₄– | –C(=O)–CH₂–CH₃ | H | H | 5.37; 8.37 |

-continued

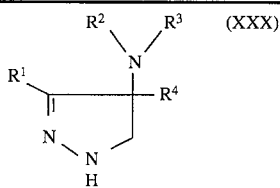

| Ex. No. | R¹ | R² | R³ | R⁴ | ¹H-NMR*⁾ |
|---|---|---|---|---|---|
| II-27 | ⌬—Br | —C(=O)—(CH₂)₃— | | H | 5.86 |
| II-28 | ⌬—F | —C(=O)—CH₂—CH(CH₃)₂ | H | H | 5.50; 8.40 |
| II-29 | ⌬—Cl | —C(=O)—CH(CH₃)₂ | H | H | 5.47; 8.35 |
| II-30 | ⌬—Br | —C(=O)—OCH₃ | H | H | 5.23; 7.79 |
| II-31 | ⌬—Br | —C(=O)—CH₃ | H | H | 5.44; 8.45 |
| II-32 | ⌬—Cl | —C(=O)—cyclopropyl | H | H | 5.48; 8.67 |
| II-33 | ⌬—Br | —C(=O)—cyclopropyl | H | H | 5.48; 8.64 |
| II-34 | ⌬—F | —C(=O)—CH(CH₃)₂ | H | H | 5.49; 8.33 |

USE EXAMPLES

In the use examples which follow, the compound listed below was employed as comparison substance:

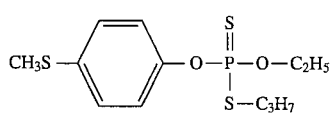

O-(4-Methylthiophenyl) O-ethyl S-(n-propyl) thionophosphate (disclosed in DE 2,111,414)

EXAMPLE A

Phaedon larvae test

| Solvent: | 7 parts by weight of dimethylformamide |
|---|---|
| Emulsifier: | 1 part by weight of alkylaryl polyglycol ether |

To prepare a suitable preparation of active compound, 1 part by weight of active compound is mixed with the stated amount of solvent and the stated amount of emulsifier, and the concentrate is diluted with water to the desired concentration.

109

Cabbage leaves (*Brassica oleracea*) are treated by dipping into the preparation of active compound of the desired concentration and infested with mustard beetle larvae (*Phaedon cochleariae*) while the leaves are still moist.

After the specified time, the destruction is determined in percent. 100% means that all beetle larvae have been destroyed; 0% means that no beetle larvae have been destroyed.

In this test, a superior activity compared with the prior art is shown, for example, by the following compounds of the preparation examples: 36, 52, 63 and 219.

EXAMPLE B

Plutella test

| Solvent: | 7 parts by weight of dimethylformamide |
|---|---|
| Emulsifier: | 1 part by weight of alkylaryl polyglycol ether |

To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by dipping into the preparation of active compound of the desired concentration and infested with cabbage moth caterpillars (*Plutella maculipennis*) while the leaves are still moist.

After the specified time, the destruction is determined in percent. 100% means that all caterpillars have been destroyed; 0% means that no caterpillars have been destroyed.

In this test, a superior activity compared with the prior art is shown, for example, by the following compounds of the preparation example: 106 and 223.

We claim:

1. A substituted pyrazoline of the formula

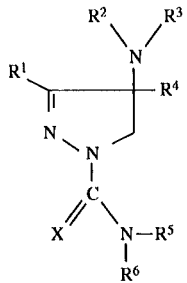

(I)

in which $R^1$ represents phenyl substituted by halogen or alkyl, and either $R^2$ represents a radical of the formula —CO—$R^7$ and $R^3$ represents hydrogen or alkyl or $R^2$ and $R^3$ together with the nitrogen atom to which they are bonded form a heterocycle represented by the formula

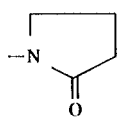

$R^4$ represents hydrogen or alkyl, $R^5$ represents hydrogen or alkyl, $R^6$ represents optionally substituted cycloalkyl or 3,4-disubstituted phenyl wherein the substituents are halogen, haloalkyl or haloalkoxy, X represents oxygen or sulfur, and $R^7$ represents hydrogen, alkyl or optionally substituted phenyl wherein the substituents are alkyl or halogen.

2. A substituted pyrazoline according to claim 1, the compound having the formula

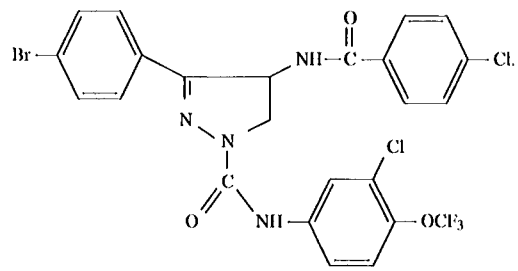

3. A substituted pyrazoline according to claim 1, the compound having the formula

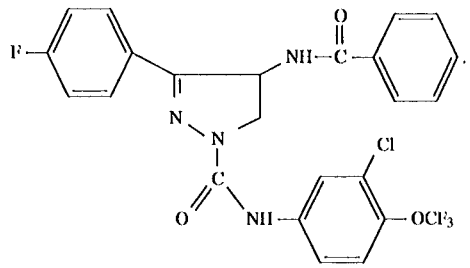

4. A substituted pyrazoline according to claim 1, the compound having the formula

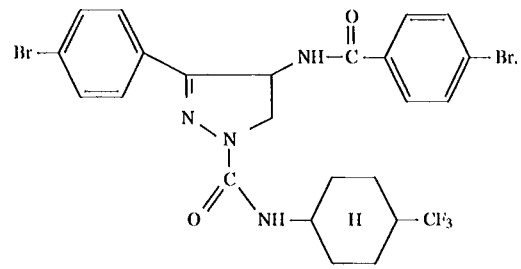

5. A substituted pyrazoline according to claim 1, the compound having the formula

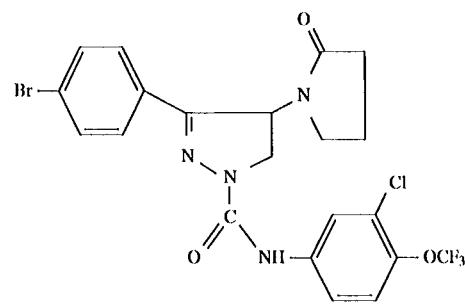

6. A substituted pyrazoline according to claim 1, the compound having the formula

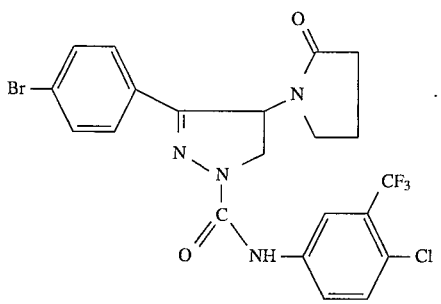

7. A substituted pyrazoline according to claim 3, the compound having the formula

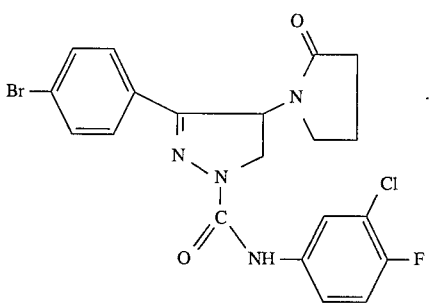

8. A substituted pyrazoline according to claim 4, the compound having the formula

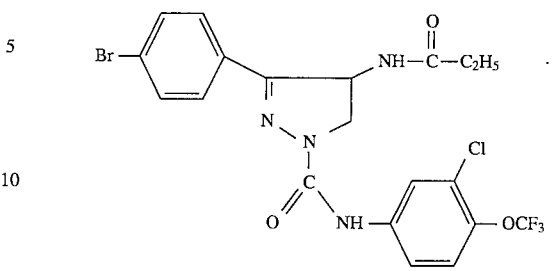

9. A pesticidal composition comprising a pesticidally effective amount of a substituted pyrazoline as claimed in claim 1, and an inert diluent or carrier.

10. A method of combatting animal pests which comprises allowing a compound according to claim 1 to act on an animal pest and/or its environment.

* * * * *

Adverse Decisions in Interference

Patent No. 5,525,622, Johannes Kanellakopulos, Rainer Fuchs, Christoph Erdelen, SUBSTITUTED PYRAZOLINES, Interference No. 103,975, final judgment adverse to the patentees rendered December 8, 1997, as to claims 1-10.

*(Official Gazette April 21, 1998)*